(12) United States Patent
Widge et al.

(10) Patent No.: US 11,241,188 B2
(45) Date of Patent: Feb. 8, 2022

(54) SYSTEM AND METHODS FOR MONITORING AND IMPROVING COGNITIVE FLEXIBILITY

(71) Applicants: The General Hospital Corporation, Boston, MA (US); Trustees of Boston University, Boston, MA (US)

(72) Inventors: Alik Widge, Somerville, MA (US); Emad Eskandar, Swampscott, MA (US); Darin Dougherty, Wellesley, MA (US); Uri Tzvi Eden, Medford, MA (US); Xinyi Deng, Boston, MA (US); Ali Yousefi, Brookline, MA (US); Angelique Paulk, Brighton, MA (US)

(73) Assignees: The General Hospital Corporation, Boston, MA (US); Trustees of Boston University, Boston, MA (US)

( * ) Notice: Subject to any disclaimer, the term of this patent is extended or adjusted under 35 U.S.C. 154(b) by 616 days.

(21) Appl. No.: 15/740,975

(22) PCT Filed: Jun. 30, 2016

(86) PCT No.: PCT/US2016/040368
§ 371 (c)(1),
(2) Date: Dec. 29, 2017

(87) PCT Pub. No.: WO2017/004362
PCT Pub. Date: Jan. 5, 2017

(65) Prior Publication Data
US 2018/0192936 A1    Jul. 12, 2018

Related U.S. Application Data

(60) Provisional application No. 62/186,470, filed on Jun. 30, 2015.

(51) Int. Cl.
*A61B 5/00* (2006.01)
*G16H 50/20* (2018.01)
(Continued)

(52) U.S. Cl.
CPC ............ *A61B 5/4088* (2013.01); *A61B 5/162* (2013.01); *A61B 5/316* (2021.01); *A61B 5/377* (2021.01);
(Continued)

(58) Field of Classification Search
CPC .......................... A61B 5/4088; A61B 5/0484
See application file for complete search history.

(56) References Cited

U.S. PATENT DOCUMENTS

| 2004/0230105 A1 | 11/2004 | Geva et al. |
| 2009/0292180 A1 | 11/2009 | Mirow |

(Continued)

OTHER PUBLICATIONS

International Search Report and Written Opinion for international application PCT/US16/40368 dated Sep. 30, 2016, 13 pages.

*Primary Examiner* — Joseph M Dietrich
(74) *Attorney, Agent, or Firm* — Quarles & Brady LLP

(57) ABSTRACT

A system and methods for monitoring and controlling a mental state of a subject are provided. In some aspects, a method includes receiving physiological and behavioral data acquired using the plurality of sensors while the subject is performing a task, and applying, using the data, a state-space framework to determine a plurality of decoder parameters correlating brain activity and behavior with a mental state of the subject. The method also includes identifying the mental state of the subject using the decoder parameters, and generating a report indicating the mental state of the subject. In some aspects, the method further includes generating, based on the identified mental state, a brain stimulation to treat a brain condition of the subject.

20 Claims, 17 Drawing Sheets

(51) Int. Cl.
*G16H 20/70* (2018.01)
*A61B 5/16* (2006.01)
*A61B 5/316* (2021.01)
*A61B 5/377* (2021.01)
*G16H 15/00* (2018.01)
*A61N 1/36* (2006.01)
*G06N 7/00* (2006.01)

(52) U.S. Cl.
CPC ........ *A61B 5/4064* (2013.01); *A61N 1/36139* (2013.01); *G06N 7/005* (2013.01); *G16H 15/00* (2018.01); *G16H 20/70* (2018.01); *G16H 50/20* (2018.01); *A61B 2560/0238* (2013.01)

(56) References Cited

U.S. PATENT DOCUMENTS

2011/0306846 A1    12/2011  Osorio
2013/0289385 A1* 10/2013  Lozano ................ A61B 5/055
                                                600/411

* cited by examiner 020      233

0 2 0    2 3 3

Control    Interference

Trial type:    Control (Congruent)    Interference (Incongruent)

020    233

Button press choice:
✗ Incorrect choice
✓ Correct choice

SYSTEM AND METHODS FOR MONITORING AND IMPROVING COGNITIVE FLEXIBILITY

CROSS-REFERENCE TO RELATED APPLICATIONS

This application is a U.S. National Phase of PCT Application No. PCT/US2016/0040368 filed on Jun. 30, 2016 which claims priority to, and incorporates by reference in its entirety, Provisional Application No. 62/186,470 filed on Jun. 30, 2015, and is entitled: "SYSTEMS AND METHODS FOR MONITORING AND IMPROVING COGNITIVE FLEXIBILITY."

FEDERALLY SPONSORED RESEARCH OR DEVELOPMENT

This invention was made with government support under W911NF-14-2-0045 awarded by the Defense Advanced Research Projects Agency. The government has certain rights in the invention.

BACKGROUND OF THE INVENTION

The field of the invention relates to monitoring and controlling brain conditions of patients. More particularly, the present disclosure is directed to monitoring and controlling cognitive states using behavioral and neural activity measurements.

Demonstrating the existence of meaningful relationships between behavior and neural activity is essential to understanding the brain. In particular, how the brain uses neural activity to integrate sensory inputs, control movements, facilitate learning and memory, activate and express emotions, and so forth, may provide valuable information about processes associated with disease and disease progression. Thus, decoding and stimulating neural activity to assist, supplement or suppress behavior, has been a subject of intensive investigation by behavioral and cognitive neuroscientists. Specifically, identifying brain states from neural activity would be very valuable for clinical therapies, such as brain stimulation and related technologies often attempting to treat disorders of cognition. However, it is difficult to accurately dose such therapies to meet a patient's clinical need.

Investigations into these questions has led to various multi-faceted experimental designs and have generated behavioral data with growing complexity. In addition, technological advances now allow for recording of large quantities of information from the brain at multiple spatial and temporal scales. Examples include electroencephalogram ("EEG") data using multi-channel electrode arrays placed on the scalp or inside the brain, functional data using functional magnetic resonance imaging ("fMRI") and magnetoencephalography ("MEG"), and others. However, availability of high-dimensional neural data and behavioral data, has also presented a challenge for statistical analysis and modeling. This is because presently, an understanding of the adequate representation relating features of behavioral and structures in the neural activity remains incomplete.

Traditionally, studies of neural decoding have focused on the relation between electrophysiological data and directly observable biological or behavioral signals. For example, one approach utilized place-field models to describe neural spiking activity in hippocampus as a function of an animal's position in its environment. More recently, there has been increasing interest in models relating neural activity to more general cognitive variables that influence multiple aspects of behavior and cognitive function. Understanding the structure of such variables may provide important information for determining neural disease processes and treatment. For example, deficits in cognitive flexibility have been linked to autism, obsessive-compulsive disorders and schizophrenia. However, many cognitive variables, such as cognitive flexibility, may only be observed through their influence on behavior, and are therefore difficult to link to neural activity directly. In addition, cognitive variables are often dynamic, leading to changing behavioral outcomes to stimuli through time.

Some methods have attempted to link neural data to unobserved signals using state-space modeling. In general, the state-space models utilize two equations, namely, an observation equation that describes how a hidden state/process is measured, and a state equation that defines how the underlying process evolves through time. For example, state-space modeling has been used to predict the movements of a rat from an ensemble place-cell activity. However, such approaches typically necessitate that the estimated behavioral signals are low-dimensional and directly observable during a first, encoding step. This would not be possible for abstract, cognitive state processes, as described above. Therefore, an important statistical challenge remains for understanding neural representations of cognitive state processes and estimating their dynamics through time.

In addition, for a large class of behavioral data, observed variables are non-negative with an asymmetric distribution. Moreover, their statistical measures change through the course of experiments. For example, many psychophysical tasks measure reaction time ("RT") as a dependent variable that is influenced by trial parameters. The RTs are positive random variables with right-skewed distributions. In repeated experiments, reaction times are often also dynamic, their statistics changing as a subject's psychological or cognitive state evolves through an experiment. While many statistical analyses of reaction time data assume that the data are normally distributed, the actual structure of this class of behavioral signals is generally not well described by a normal distribution.

Hence, in light of the above, there is a need for new systems and methods for monitoring and controlling cognitive states to affect behavioral and other outcomes.

BRIEF SUMMARY OF THE INVENTION

The present disclosure is directed to monitoring and controlling a subjects brain condition using brain stimulation. In particular, the present disclosure provides an important technological advancement based on a newly determined relationship between high-dimensional electrophysiological data and complex, dynamic behavioral data. As will be described, a state-space framework is utilized to correlate neural activity recorded across various brain areas and behavior to a mental state, such as cognitive flexibility, learning state, or other mental state. The foregoing and other aspects and advantages of the present disclosure will appear from the following description.

In one aspect of the disclosure, a system for monitoring a mental state of a subject is provided. The system includes a plurality of sensors configured to acquire physiological data and behavioral data from the subject, and a processor configured to receive calibration data acquired using the plurality of sensors while the subject is performing a task, and apply, using the calibration data, a state-space framework to determine a plurality of decoder parameters correlating brain activity and behavior with a mental state of the subject. The processor is also configured to identify the mental state of the subject using the decoder parameters, and generate a report indicating the mental state of the subject. The system also includes an output for displaying the report.

In another aspect of the disclosure, a method for monitoring mental state of a subject is provided. The method includes receiving physiological and behavioral data acquired using the plurality of sensors while the subject is performing a task, and applying, using the data, a state-space framework to determine a plurality of decoder parameters correlating brain activity and behavior with a mental state of the subject. The method also includes identifying the mental state of the subject using the decoder parameters, and generating a report indicating the mental state of the subject. In some aspects, the method further includes generating, based on the identified mental state, a brain stimulation to treat a brain condition of the subject.

In yet another aspect of the disclosure, a non-transitory, computer-readable medium is provided. The non-transitory, computer-readable medium includes therein instructions that, when executed by a processor, can generate a report for use in controlling a mental state of a subject. The instructions include acquiring, using the plurality of sensors, calibration data while the subject is performing a task, and applying, using the calibration data, a state-space framework to determine a plurality of decoder parameters correlating brain activity and behavior with a mental state of the subject. The instructions also include acquiring physiological data using the plurality of sensors, and identifying a mental state of the subject using the decoder parameters and acquired physiological data. The instructions further include determining, based on the identified mental state, a brain stimulation to treat a brain condition of the subject, and generating a report indicative of the brain stimulation.

In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
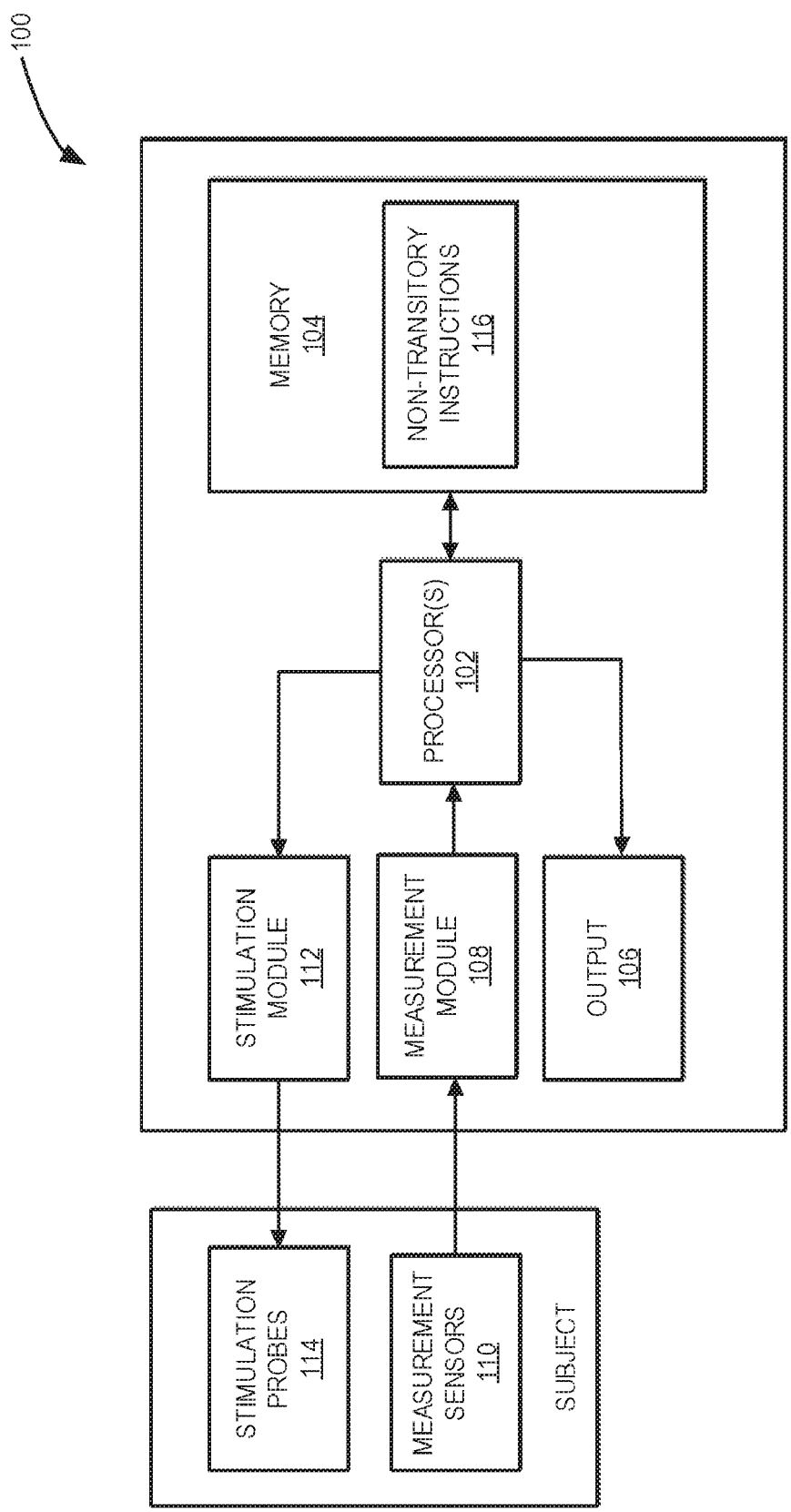
FIG. 1 is a schematic diagram of an example system, in accordance with aspects of the present disclosure.

Specifically, the present disclosure recognizes that relationships between behavior and neural activity are often very complex. As such, modeling such relationships can become an intractable problem, especially for many behavioral tasks involving multiple brain areas with a large number of recording sites. Therefore, in contrast to previous methods in which behavior and neural activity are directly linked to one other, the present disclosure introduces a novel approach that correlates neural activity and behavior with a hidden variable, such as cognitive flexibility or other mental state. By linking neural activity and behavior using a low-dimensional representation, the present disclosure allows for reduced computational burden and better suitability to implantable and other interventional devices.

As will be described, the present disclosure describes how correlations between 1) behavior and a mental state, 2) the mental state and brain activity, and 3) changes in the aforementioned due to electrical or other stimulation of the brain may be determined. Using measured behavioral and physiological signals, moment-to-moment estimates of a mental state, such as cognitive flexibility or an indication thereof, may be obtained, allowing brain stimulation for the treatment of a subject suffering from a mental illness or other brain condition. In particular, because cognitive flexibility is strongly associated with mental illnesses, the present approach may not only be used for determining an optimal brain stimulation to a subject, but also be helpful in understanding how to choose patients who should receive such treatment.

In some aspects, a framework based on a state-space approach is provided herein, correlating a mental state to various behavioral observations. A generalized linear model ("GLM") may then be used to decode the neural activity into a neural ensemble given the mental state. This may include a point-process GLM in the case where the neural ensemble is composed of the recorded discrete activity of individual brain cells. Using the decoding mechanism, a brain stimulation may then be developed that can manipulate the brain activity and relieving the symptoms of mental illness or other brain condition. In some embodiments, the present approach may be used a "closed-loop" system configuration, whereby electrical activity from a network of brain areas is acquired and used as feedback to determine a stimulation configured to correct abnormal or undesired electrical activity associated with those brain networks.

Herein, a mental state generally refers to any brain state of a subject, which include may include a fear state, such as a fear extinction state, a negative affect state, or a somatosensory state, a reward motivation state, such as a positive affect state, a negative affect state or a somatosensory state, an emotional regulation state, a decision making state, an impulsivity state, an attention state, a perseveration state, a cognitive state or cognition state, such as a learning or memory state, and other mental states.

Generally, behavioral tests are widely used to quantify features of cognitive processing. However, for a large class of behavioral signals, the observed variables are dynamic and do not follow normal distribution models. For instance, reaction times in psychophysical tasks are always positive, which is not well-captured by a normal distribution. As a result, classical estimation algorithms are ill-suited to modeling such data. Therefore, in some aspect of the disclosure, non-Gaussian formulations may be used to estimate a mental state from behavioral signals. For instance, a behavioral signal conditioned on the mental state may follow a Gamma distribution. Also, a behavioral signal containing a Binary response conditioned on the mental state may follow a Bernoulli distribution. Using an approximate expectation-maximization ("EM") algorithm, both the mental state, its parameters, and parameters associated with the Gamma and Binomial distributions may be determined. This approach is in contrast to previous state-space models applied to neural data, these having been applied to data that only included point processes (e.g. Poisson) or normal distributions.

As appreciated from descriptions below, the herein described system and method provide important and clinically useful technological advancements for treatment of various brain conditions or mental illness, such as psychiatric disorders, including depression, obsessive-compulsive disorder, post-traumatic stress disorder ("PTSD"), major depressive disorder ("MDD"), generalized anxiety disorder ("GAD"), traumatic brain injury ("TBI"), substance use disorder ("SUD"), borderline personality disorder ("BPD"), pain disorder ("PD") and others. In particular, brain markers and how they relate pathological behavior may be identified in order to provide relief for mental illness and other brain conditions.

Turning now to FIG. 1, a schematic diagram of an example system 100, in accordance with the present disclosure, is shown. In some embodiments, the system 100 may be a deep brain stimulation device, or other interventional or wearable device used for monitoring and treatment of a brain condition of a patient. In other embodiments, the system 100 may be a personal computer, a workstation, laptop, tablet or other general purpose computing device. In addition, the system 100 may operate as part of, or in collaboration, with a computer, system, device, machine, mainframe, or server. In this regard, the system 100 may be any system that is designed to integrate with a variety of software and hardware capabilities and functionalities, in accordance with aspects of the present disclosure, and may be capable of operating autonomously, semi-autonomously, or in a closed-loop mode of operation.

In general, the system 100 includes one or more processors 102, a memory 104, an output 106. The system 100 also includes a measurement module 108 configured to acquire physiological and behavioral data from a subject using measurement sensors 110 coupled thereto. In some implementations, the system 100 also includes a stimulation module 112 configured to deliver a brain stimulation to the subject using one or more stimulation probes 114 coupled thereto. In particular, the stimulation probes 114 may be configured to deliver the brain stimulation by way of voltage or current signals, or both.

In some embodiments, the measurement sensors 110 may be configured for capturing a subject's behavior. By way of example, the measurement sensors 110 can be in the form of a keyboard, mouse, joystick, touch screen, number pad, a camera and other user interface or input devices. Using such sensors, behavioral data may be acquired from a subject while actively or passively performing a task. In other embodiments, the measurement sensors 110 may be configured to measure a brain activity or other physiological activity of the subject. By way of example, the measurement sensors 110 can include electric probes or contacts, such as electroencephalogram ("EEG") probes, configured to measure neural signals associated with the subject's brain activity. Such measurement sensors 110 may be wearable or implantable, or both.

In addition to being configured to carry out steps for operating the system 100, the processor 102 may also be configured to monitor and control a mental state of a subject by carrying out transitory and non-transitory instructions 116 stored in the memory 104. In some aspects, the processor 102 may be configured to direct the acquisition of physiological and/or behavioral data. Specifically, the processor 102 may be configured to acquire calibration data, which may include both behavioral and physiological data, while a subject is performing a task. Tasks may be provided via output 106, in the form of using audio or visual instructions or both. For example, tasks can include tracking a target displayed on a screen, identifying an object physically or verbally, touching a particular region of a touch screen, using a mouse, manipulating objects, and so forth. In some aspects, a task may be adapted by the processor 102 based upon a patient's condition or feedback, determined mental state, or based on input from a supervising clinician.

In accordance with aspects of the disclosure, the processor 102 may be configured to apply a state-space framework to determine a plurality of decoder parameters correlating brain activity and behavior with a mental state of the subject, as will be described. The processor 102 may then identify the mental state of the subject using the decoder parameters. In some aspects, during or upon completion of a given task, the stimulation module 104 can generate a brain stimulation to be delivered by the stimulation module 114 to more than one brain tissues or brain regions in the form of electrical signals configured to stimulate the selected tissues or regions in order to enable or enhance performance of the current task, or a future task. In some aspects of the disclosure, brain stimulation may be performed to improve a mental state, such as cognitive flexibility, of a subject as described.

The processor 102 may also be configured to generate a report provided via output 106. The report may include a variety of information, including a present and/or future mental state of the subject, information and/or parameters associated with a generated brain stimulation, and so forth.

As shown in FIG. 1, the system 100 includes a memory 104 including therein a non-transitory, computer-readable medium with instructions that, when executed by the processor 102, can generate a report for monitoring and/or controlling a mental state of a subject. Processing instructions may include acquiring calibration data to be used in a state-space framework determining decoder parameters correlating brain activity and behavior with a mental state. The instructions may also include identifying the mental state using the decoder parameters, and determining, based on the identified mental state, a brain stimulation to treat a brain condition of the subject. In some aspects, the instructions include generating a report indicating the brain stimulation. The report may include other information, as detailed above.

Figure 2C:
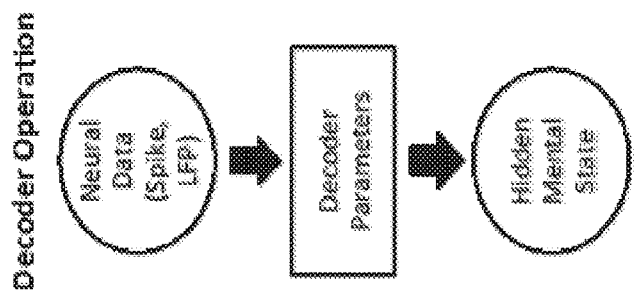
FIG. 2C is a schematic illustration showing the operation and application of a neural decoding model, in accordance with aspects of the present disclosure.
Figure 2B:
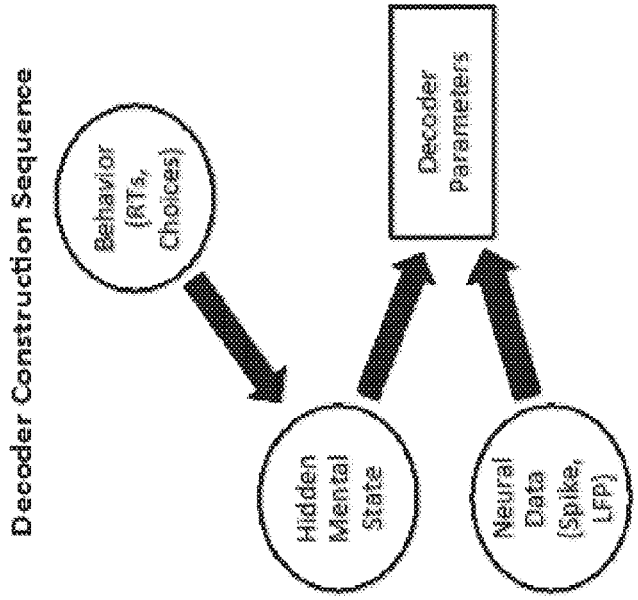
FIG. 2B is a schematic illustration showing how the behavioral portion of the causative model may be inverted, through the state-space framework, to obtain a neural decoding model, in accordance with aspects of the present disclosure.
Figure 2A:
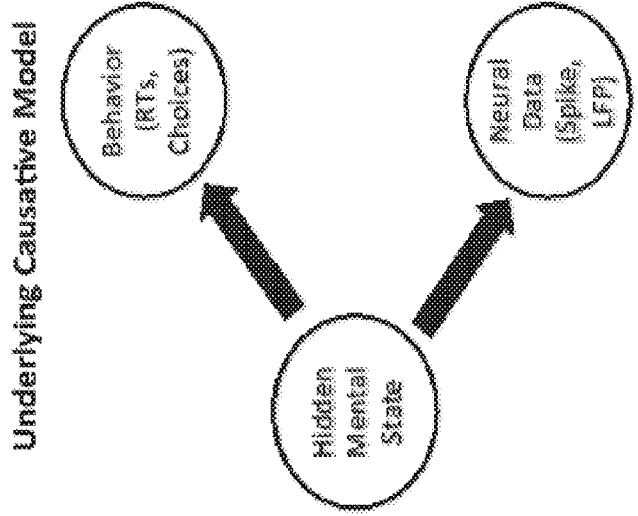
FIG. 2A is a schematic illustration showing a causative model, in accordance with aspects of the present disclosure.
Figure 3:
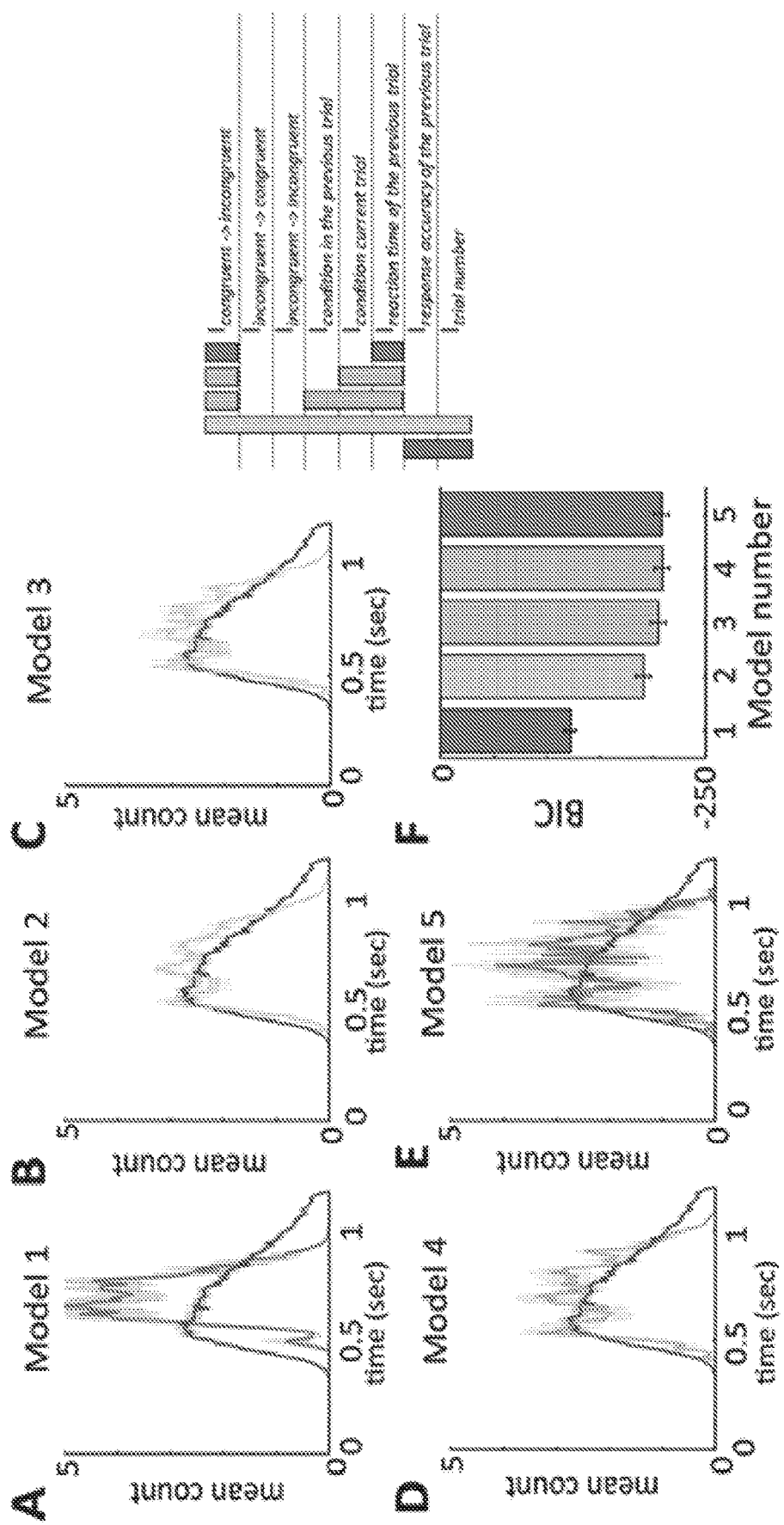
FIG. 3A-F are graphs showing a series of example models (A-E) fit to neural data and reaction time behavioral data from a large dataset of patients being compared using a Bayesian Information Criterion ("BIC") (F).

The following description details a modeling approach, in accordance with aspects of the present disclosure, and gives a non-limiting example of operation using multiple source interference task ("MSIT") behavioral data and neural data. Referring specifically to FIG. 2A, the present approach hypothesizes that a mental state may be simultaneously reflected in neural activations and observable psychophysical variables, and could be inferred from either given knowledge of the encoding model. That is, rather than directly link behavior and neural data, as typically performed in previous techniques, a low-dimensional mental state reflecting behavior and neural activity may be identified. This implies that conditioned on knowledge of the mental state or latent state, behavior and neural activity have no further mutual information. That is, the state variable at any given time summarizes all aspects of the neural activity that are relevant for predicting upcoming behavior.

The challenge is therefore to infer a hidden mental state by inverting the relationships between behavior, neural activity, and mental state, and to identify a decoder that can recover the latent variable(s) from neural activity alone. Specifically, a decoding algorithm is produced by parameterizing ("calibrating") the relationships between the mental state and behavior, and the mental state and neural activity, as shown in FIG. 2B. That is, the mental state may be inferred from behavior for multiple timepoints in a block of calibration data. That inferred mental state and neural data can then be combined in a generalized regression model to infer optimal parameters for decoding. In a decoder operation, performed in a real-time, untethered mode, the obtained parameters may be used to infer the hidden mental state directly from brain activity. No further task-related behavioral data are needed until the patient or clinician chooses to re-calibrate. The hidden mental state may then be monitored and controlled using brain stimulation. This approach may be summarized in the following four steps:

1. Model Selection. Identify a psychologically grounded model for how hidden state variables may influence behavior on a given task, verifying that this model explains the observed behavioral data adequately and that the resulting state variables have clinical implications for closed-loop control.

2. Behavioral Decoding. For each instance of a subject performing a block of the task, simultaneously fit the optimal parameters of this model and estimate the most likely value of the hidden state given those parameters.

3. Encoding. Using the state estimate decoded from behavior, understanding of the involved brain areas, and a statistical model of the relationship of neural firing to covariate(s), identify the neural features with strong correlation to the hidden state estimate.

4. Decoding. Define an algorithm (which may be one of several transforms, see below) that inverts the encoding relationship to infer the hidden state that is most likely given a subset of the neural data.

In the following description, these steps are used to estimate the hidden mental state of a single domain, Cognitive Flexibility, as encoded in behavior and neural activity during the Multi-Source Interference Task ("MSIT"). The feasibility is demonstrated for decoding flexibility from simultaneously recorded behavior and local field potential ("LFP") data from epilepsy monitoring unit ("EMU") patients performing the MSIT. However, one of ordinary skill would readily recognize that the present disclosure is not limited to this implementation.

Figure 5:
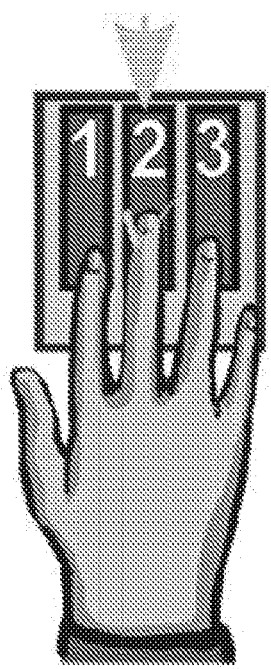
FIG. 5 is an illustration showing example stimuli for a multiple source interference task ("MSIT") shown including non-interference (control) and interference conditions, in accordance with aspects of the present disclosure.
Figure 5:
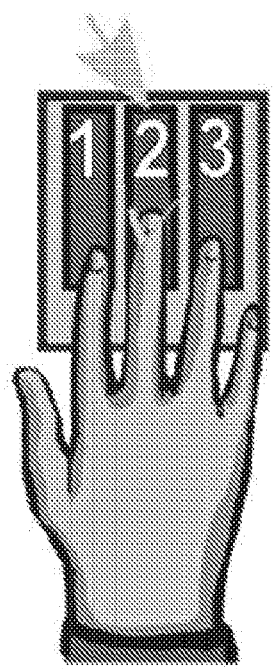

Specifically, the MSIT is designed to evoke high levels of cognitive conflict and require subjects to actively engage top-down control throughout the task. In particular, the MSIT task generates objective behavior that measures an otherwise un-observable cognitive flexibility state. Example stimuli are shown in FIG. 5. Three sources of cognitive interference combine in this task. First, flanker: in control conditions, the flanking distractors are always "0", which is not a valid response. In interference conditions, distractors are also valid targets. Second, Stroop: the target response ("2" in the figure) is placed out of its intuitive position as the second number in the sequence. The value of the digit (2) thus conflicts with reporting of the position (1). This interacts with the third source of interference, motor. Subjects are required to respond with the index, middle, and ring finger of the right hand. In the example, there is a highly prepatent response to press with the index finger, corresponding to the position in which the "2" appears. However, only a press with the middle finger (the "2" digit and "2" key) will be scored correct.

The MSIT, as with other Stroop-like tasks, requires not only top-down control on individual trials, but also substantial trial-to-trial adaptation. In particular, while cognitive interference slows reaction time ("RT"), that slowing changes depending on the preceding trial. Interference trials that immediately follow a non-interference trial show a larger RT change (relative to baseline) than interference trials that follow another interference trial. The precise mechanism remains a matter of debate, with some authors suggesting that sequence-dependent RT changes may represent acquisition of a response bias, rather than improved function of a conflict-monitoring mechanism. However, either explanation highlights the fact that MSIT performance requires mental flexibility. Because the desired response is constantly changing, as is the trial type, there is no response bias that can improve performance. As a result, subjects must engage in constant self-monitoring and adaptation. For subjects with decreased capacity for that adaptation, the increased need for flexibility is reflected in longer RTs.

The modeling approach, in accordance with aspects of the present disclosure, is now described. Specifically, for any behavioral task performed by a subject, continuous-valued (i.e. reaction time, skin conductance) and binary-valued (yes/no or high/low choices) behavioral data may be obtained. To develop a model of how the hidden mental state(s) are encoded in those behavioral data, how trial features affect the behavior must be first defined. The goal is a model where an individual subject's trial-to-trial outputs can largely be expressed as a function of variables such as trial difficulty, available reward, and so forth. Herein it is assumed that all linkages between the hidden state and observable behaviors can be captured with a generalized linear model ("GLM").

For a continuous behavior Z (such as reaction times) with A covariates that do not interact with the hidden state $x(t)$ and B covariates that do interact the following relationship may be written:

$$\mu(t) = \beta_o + \sum_{a=1}^{A} \beta_a I_a(t) + \sum_{b=1}^{B} \beta_b x(t) I_b \qquad (1)$$

$$z(t) = f(\mu(t), \sigma)$$

where $\mu$ represents the expected value of the behavior given the model and I is an indicator function for any given trial feature (nature of the choice offered, value of a reward, affective valence, and so forth). Also, f may be any function, such as the identity or an exponential link. Binary choices are similar, but f could be a logistic.

Psychological theory often offers numerous explanatory variables. For instance, for the univariate case of reaction time ("RT") on the MSIT, the RT model may include:

$\beta_0$, the patient's inherent psychomotor speed (intercept)
$\beta_1$, the effect of cognitive interference in the current trial
$\beta_{t-1}$, cognitive interference from the previous trial
$\beta_{err}$, error-induced slowing (in response to an error on the previous trial)
$\beta_{AR}$, the previous RT (an autoregressive model accounting for slow time-varying factors such as fatigue)

History-dependence terms that consider not just the interference type of the present trial, but the type of preceding trials. This is the well-known "Gratton Effect", where behavioral adaptation appears to be mediated by structures also involved in severe psychiatric illness. These have forms such as $\beta_{IC}$, which would model the RT change for switching from an (I)ncongruent to (C)ongruent trial.

Some of these indicators will be redundant, and others may show only weak correlations to RT. Therefore, a preliminary step is model selection: testing a series of alternate models M. At this point, with less interest in the specific value the hidden mental state, and more in which covariates best explain the observed behavioral data, the hidden state $x(t)$ may temporarily be removed from models. Their parameters may then be estimated, and their performance may be evaluated in terms of the data likelihood function penalized by the number of terms K and timepoints T:

$$m = \arg\min[-2 \log(p(Z|m^*, \Theta_m)) + K_m \log T]$$

$$\log(p(Z|m^*, \Theta_m)) = \Sigma_{t=1}^{T} \log(f(\mu(t, m^*, \Theta_m) - f^{-1}(Z(t)))) \qquad (2)$$

This process is illustrated for the MSIT, as shown in the example of FIGS. 3A-F. Specifically, FIGS. 3A-F show fitting of multiple putative models (A-E) using data from a large dataset of patients (compared using a Bayesian Information Criterion ("BIC") (F). The RT data were fit well with only 4 parameters, and even 2 parameters were able to capture a substantial fraction of variance. Additionally, a model with two-trial history dependence, the current-trial interference level, and previous trial reaction time offered the best parsimony-fit tradeoff, assuming a specific penalty term. The BIC was used here to compare models because it affords models with fewer parameters than the alternative Akaike information Criterion. Other model-selection criteria could also be used without loss of generality. An important reason to reduce the dimensionality is that the above approach can be used in a system as described with reference to FIG. 1, whereby minimizing power consumption is advantageous. By reducing the number of calculated parameters to decode behavior and neural data, the number of calculations may be optimized and mitigate the dimensionality problem.

Importantly, although a model was herein constructed to account for the hidden state, initial model-fitting does not directly model that state. Because the state is a time-varying (trial-to-trial) quantity, this first analysis may not properly account for it, which takes place on whole blocks of data. Adding the hidden mental state is the next step of behavior decoding.

Behavior decoding for inferring a hidden state is now described. Specifically, once a model (or handful of alternates) that adequately captures whole-block behavior is identified, as described above, the model may be then modified to explicitly consider the hidden mental state. For the case of identifying Cognitive Flexibility as expressed in the MSIT, a hidden state $x(t)$ can be defined that multiplies model terms that plausibly require that flexibility. This is most evident in the congruent→incongruent switches, where a subject is required to adapt to a much harder problem than a preceding trial. The GLM incorporating x, derived from Model 4 of FIG. 3D, becomes:

$$RT(t) \sim N(\mu(t)\sigma)$$

$$\mu(t) = \beta_0 + \beta_I I_{congruent} + \beta_{CI} x(t) I_{CI} + \beta_{IC} x(t) I_{IC} + \beta_{AR} Z(t-1) \qquad (3)$$

Because the indicator functions I are defined on a per-trial basis, the first step is to infer x on that same time scale—one point per trial, aligned with measurement of the behavioral variable(s) Z. For an MSIT example where data consists of single continuous-valued output of reaction times, that inference can be reduced to Kalman filtering ("KF"). While the MSIT can also include correct/incorrect responses, these can be non-informative if subjects are pre-trained to well over 90% correct before data collection begins. RT therefore can contain the majority of information about the hidden state.

For other behavioral tasks where a subject's responses are also a function of the hidden state (gambling, reward learning, and other probabilistic decision-making tasks), the present approach can be generalize using mixed continuous/ point-process filtering approach. This was originally demonstrated on associative learning, but can apply to any domain or state given the correct encoding model between behavior and state.

For the MSIT, key Kalman equation and matrices to estimate the hidden state may then be:

$$x_{t|t-1} = F_t x_{t-1|t-1} + Bu_t \quad (4)$$

$$F_t = \begin{bmatrix} 0 & 0 \\ A & 0 \\ AI_{CI,t} & 0 \end{bmatrix}$$

$$B = \begin{bmatrix} 0 & 0 \\ I & 0 \end{bmatrix}$$

$$u = [I_{CI,t} \ Z_{t-1} \ I_{i,t} \ 1]$$

where A represents the dynamics of the hidden state over time. A core assumption of this approach is that psychological states are relatively static trial-to-trial and even within a block unless acted upon by outside forces (physical or mental fatigue, stress, or brain stimulation). Therefore, A can be set to 0.99 for these experiments, while noting that more complex models (e.g., inherent oscillatory dynamics of the hidden state) could easily be accommodated in this same framework. From these, the KF can be iterated in the forward, (state estimation) and backward (smoothing) directions offline to estimate x(t) for each trial. The state and noise covariances and R can be estimated from the whole-block GLM fit:

$$Q = R = \frac{1}{T} \sum_{t=1}^{T} (\hat{Z}_t - Z_t)^2 \quad (5)$$

This effectively apportions the variance between the GLM's estimate and the observations equally between the hidden state and general noise in the subject's motor response, a reasonable assumption in the absence of prior information.

Figure 4A:
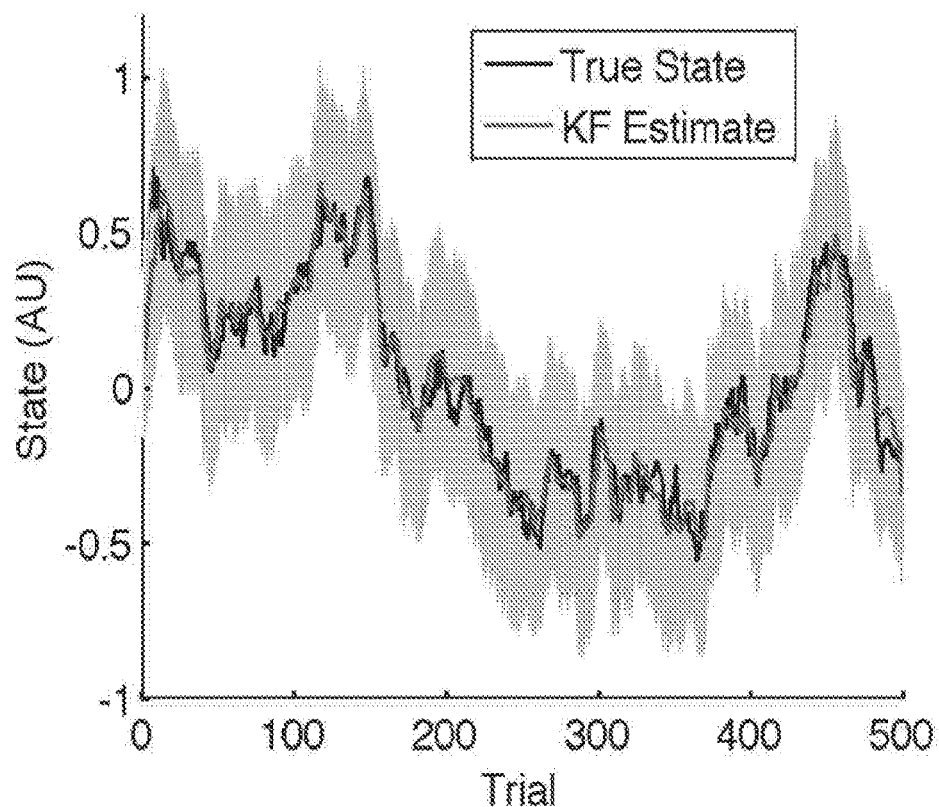
FIG. 4A is a graph demonstrating that, on simulated data, the present state-space estimation framework correctly recovers an underlying latent variable from behavioral data, in accordance with aspects of the present disclosure.

To verify the validity of this approach, MSIT reaction time data was simulated following the reduced GLM, and the hidden state $x_t$ was generated as $x_{t+1} = Ax_t + N(0, 0.05)$ with $x_1 = 0.5$. Five hundred instantiations of this system were simulated for 500 trials each. To estimate the KF's performance in real-world situations where starting states are not well known, the filter seed was deliberately mis-specified as $x_1 = 0$. FIG. 4A shows an example from one simulation, verifying accurate recovery of the hidden state despite this mis-specification. Across 500 simulations, the mean normalized RMS error of state estimation was approximately 3.69%, with a standard deviation of approximately 19.6%. This was largely driven by a handful of outlier cases in which the filter estimated the state dynamics correctly, but had a constant offset relative to the actual state. In practice, this could be straightforwardly detected and corrected by examining the reaction time residuals, which would show a substantial low-frequency/DC component inconsistent with the expected white-noise process.

Figure 4B:
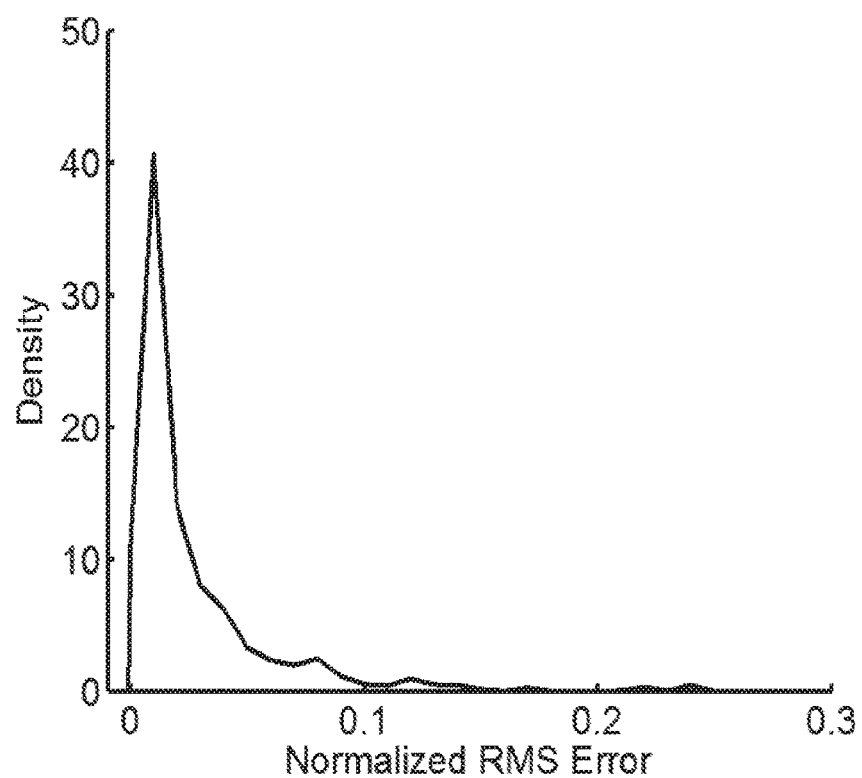
FIG. 4B is a graph showing normalized root mean square ("RMS") error for the estimation shown in FIG. 4A, demonstrating that this error is close to 0 for most timepoints.

The above approach makes the standard KF assumption that variance in the data follows a Gaussian distribution, enabling Gaussian uncertainty propagation. As seen in FIG. 4B, this is a reasonable approximation for RT data on the MSIT. For RT on other tasks, or for underlying binomial parameters in the case of response data, this may not hold. For instance, since behavioral data are often non-negative and may have a "long tail", they are often more accurately described by a Gamma distribution. If this situation arises as various domains are modeled, it can readily be handled. First, use of the linear KF on an augmented state may be continued whereby a Gamma dispersion parameter v is tracked as a state variable. Second, the Extended Kalman Filter or other local-linearization techniques may be readily utilized, where the necessary derivatives can be analytically computed.

After estimating the hidden state from behavior, it may be considered to be "ground truth" for developing a neural decoder, as described below. This approach is equivalent to the known trajectory of a training cursor or endpoint trajectories being under arm/hand control. Then, a link with the observed neural data may be obtained using a GLM approach, as follows:

$$LFP_{c,f} \sim \text{Gamma}(\mu_{c,f}, v), \ \mu_{c,f} = \sum_{i=1}^{\|x\|} \beta_{c,f,i} x_{i,t}, \ \text{Var}(LFP_{c,f}) = v\mu_{c,f}^2 \quad (6)$$

and/or $$p(\text{spike}_c) \sim PP(\lambda_c), \ \lambda_c = \sum_{i=1}^{\|x\|} \beta_{c,i} x_{i,t}$$

where c indexes channels, f frequency bins of a power decomposition, i includes elements of the state vector, and t is time. This can be considered as whole-trial features, which may be more realistic for a closed-loop algorithm doing infrequent state estimation. It could also be decomposed to a finer time resolution by interpolating the state variable, for instance, using cardinal splines.

Figure 6:
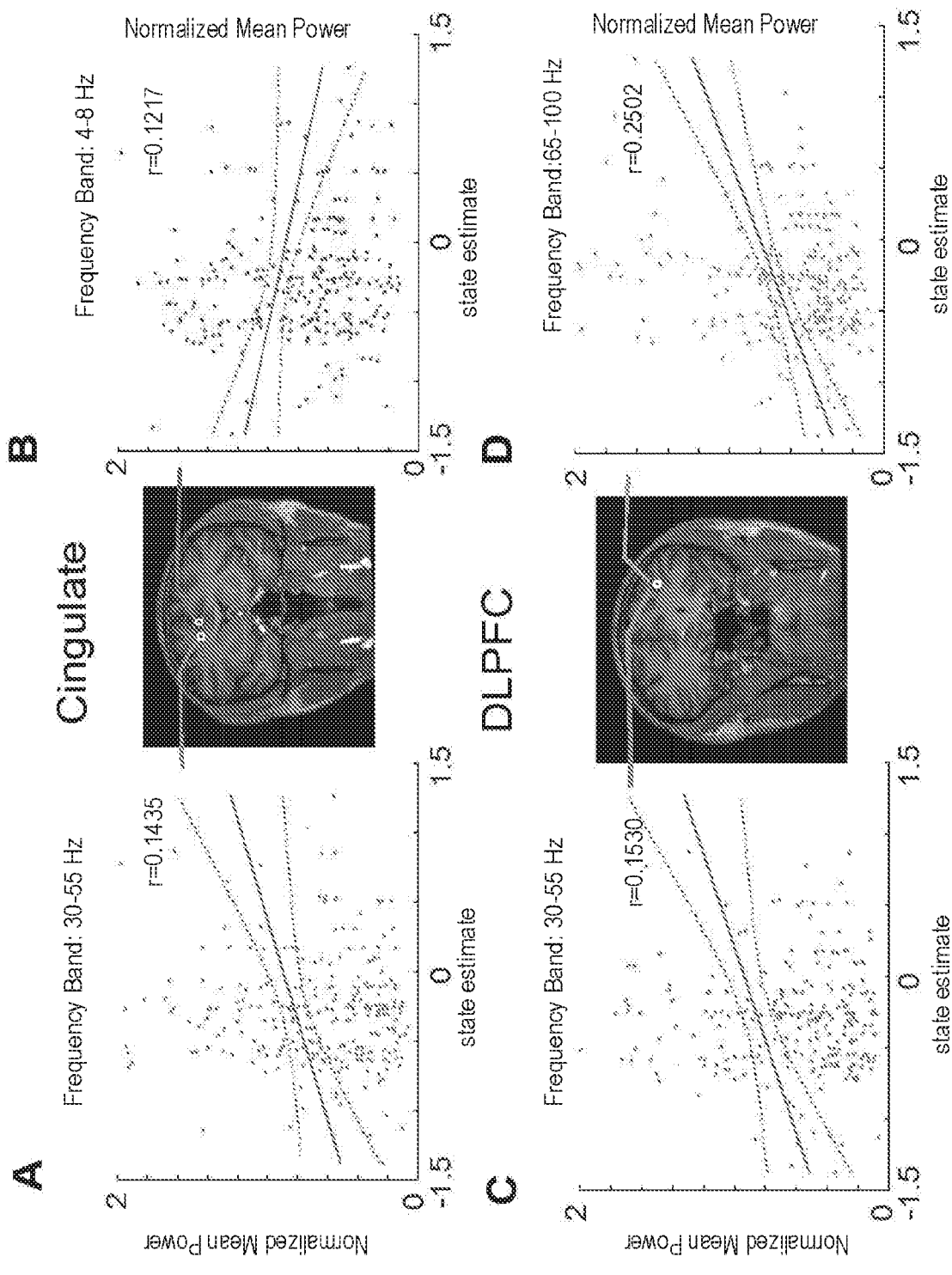
FIG. 6 are graphs illustrating a correlation analysis between a hidden cognitive flexibility state estimated based on an epileptic patient's reaction time and correct/incorrect choices while performing a MSIT and measured local field potential ("LFP") features.

For the hidden state based on the MSIT behavior, or any other scalar x, this reduces a complex problem of associating hidden state with multidimensional neural activity data to a simple correlation analysis. Local field potential ("LFP") channels/frequencies can be rank-ordered in terms of their correlation with the state, as shown in FIG. 6. In particular, FIG. 6 shows a correlational analysis between a hidden Cognitive Flexibility state (inferred by Kalman filter on behavior) and LFP features in a single epilepsy monitoring patient performing the MSIT. All analyses represent correlations between the hidden state's value on a given trial and the value in a specified LFP power band at a single electrode directly before the subject's response on that trial. In the figure, we show only electrodes/bands with significant correlations to the hidden state, where significance is defined as $p < 0.05$ using a t transformation of the correlation coefficient. The solid line represents the line of best fit, whereas dotted lines give uncertainty bounds. (A-B), right dorsal cingulate, an area commonly activated by the MSIT. (C-D), left dorsolateral prefrontal cortex, also activated by MSIT and implicated in major depression. In all cases, correlation between individual neural features and the hidden state are weak, implying that the correct solution is multi-area combined decoding. This analysis treats each channel and frequency band as independent. In practice, there is substantial correlational structure between neighboring frequencies and sometimes between LFP channels depending on the electrode type. This can be resolved during the dimension reduction built into the decoder construction, described next.

Feature selection presents a challenge for developing the encoding-decoding model. Particularly when fully frequency-decomposed LFP and multiple time lags from a potentially large number of electrode recordings, and correlational effects are considered, overfitting the data is a substantial concern. This increases when we consider inter-electrode or inter-area features, such as cross-frequency interactions, coherence/coherency, or derived graph metrics. Therefore, in accordance with aspects of the present disclosure, a stepwise decoder-building process may be utilized, with steps follows:

1. Identify the dispersion parameter 8 over the entire dataset Y, given as the ratio of the variance to the mean across channels.
2. While BIC continues to decrease, select the $k^{th}$ neural feature by:
    a. For each candidate neural feature:
        i. Identify the maximum-likelihood $\beta$ to encode the hidden state across all T timesteps.
        ii. Calculate BIC as $-2 \log p(X|\beta, Y) + k \log T$
    b. If BIC decreases from step k−1, select the feature that minimizes BIC. Otherwise, stop with k−1 features in the decoder.

This stepwise process has two important features. First, it produces a decoder that fits the state estimate and data using the smallest number of neural features. This is advantageous for a lightweight algorithm that has to run on a low-power system. Second, it automatically handles dependency between adjacent channels or frequency bands. Once a feature is selected, adding further features with high correlation to that selection can remove very little residual error from the state estimate. BIC's strong penalty term ensures that the stepwise process selects a relatively independent set of channels.

The resulting decoder can be used in any Kalman-like process for on-line state estimation from neural data alone, without concomitant behavioral data. However, to maintain accuracy across days, re-calibration can then be done whenever the patient is able to perform another block of the behavioral task. It is also possible, via an augmented state approach, to handle situations in which v is time-varying, although we do not believe this will be necessary.

The linear formulation described above may provide a limited uncertainty in the state estimate or the decoder, via the variances of the GLM parameters $\beta$ and the state covariance P derived during the online KF operation. Although these can handle the case of Gaussian probability densities, a true psychological state estimate may likely have a more complex probability landscape. Therefore, a non-linear framework may be used to estimate that full probability density function ("PDF"). Specifically, to decode Cognitive Flexibility state x from LFP Y across C channels and decomposed into F frequency bands, the following formalism may be used:

$$p(x_t | Y_t) = \frac{p(Y_t | x_t) p(x_t)}{p(Y_1)} \quad (7)$$

$$p(x_1) = p(x_{t|t-1}) = A p(x_{t-1})$$

$$p(Y_t | x_1) = \prod_{c=1}^{C} \prod_{f=1}^{F} \text{Gamma}(\beta_{c,f}, x_t, v)$$

where subscripts t, c, and f index time, channel, and frequency band, respectively importantly, for practical decoding, one need not necessarily compute the $p(Y_t)$ term at each timestep. Because it is identical across the support of $x_t$'s PDF, the prior data likelihood may be just a normalizing factor and not necessary for tracking the probability envelope of x. If it is substantially non-uniform and required to guide state estimation, it can also be computed intermittently, such as every n timesteps. In a practical implementation, one may not wish to compute the conditional probability of every element of the LFP vector $Y_t$, given that most will have minimal dependence on the hidden state. The stepwise model-building process above can again be used to identify a small subset of useful neural data, and decoding may then be performed only on that subset.

In summary, three possibilities for estimating a hidden Cognitive Flexibility state from MSIT data have been described, namely from behavior (which could be done on-line via the Kalman filter without the smoothing step), from neural data via a linear-Gaussian model, and from neural data via a Bayesian model. All three could support early experiments in closed-loop control of psychiatric state.

Figure 7:
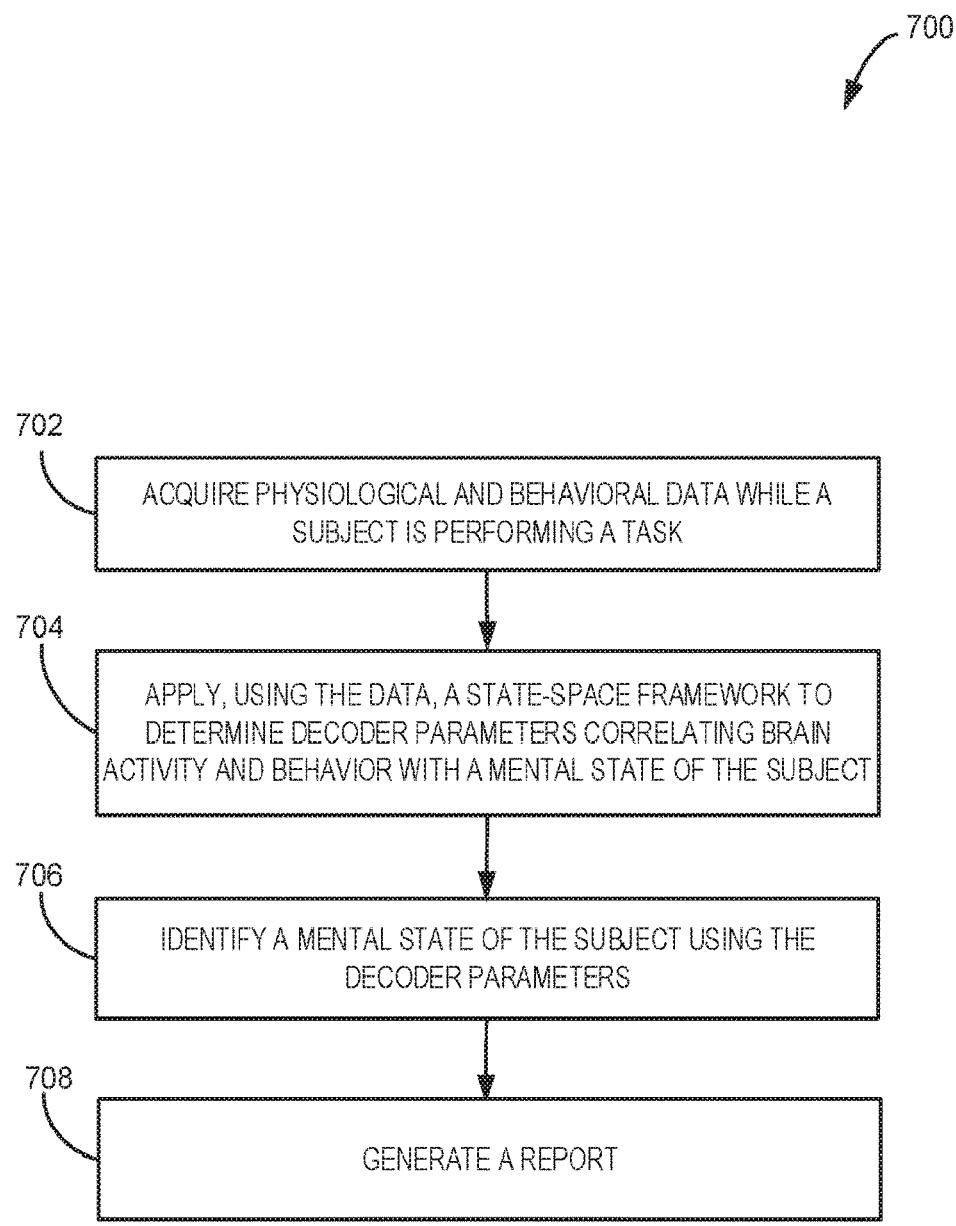
FIG. 7 is a flowchart setting forth steps of a process, in accordance with aspects of the present disclosure.

Referring now to FIG. 7, a flowchart setting forth steps of a process 700 for identifying a mental state of a subject, in accordance with aspects of the present disclosure, is shown. The process 700 may be carried out using a system as described with reference to FIG. 1, or any other suitable system, device or apparatus. Specifically, the process 700 may begin at process block 702 with receiving physiological and behavioral data acquired using the plurality of sensors while the subject is performing a task. For instance, the data may be retrieved from a memory, database, server, or other data storage location. In some aspects, the data may be acquired at process block 702, as described. The acquired or received data may then be applied in a state-space framework, as described, to determine a plurality of decoder parameters correlating brain activity and behavior with a mental state of the subject, as indicated by process block 704. As described, the mental state may include a cognitive flexibility, and other mental states.

At process block 706, a mental state of the subject may then be identified using the decoder parameters, in accordance with descriptions provided. Then, at process block 706, a report of any form may then be generated indicating the identified mental state of the subject. Process blocks 702-706 may be repeated for a number of times, as desired, allowing for moment-to-moment monitoring the subject's mental state. In some aspects, a brain stimulation may be determined or generated, based on the identified mental state(s), where the brain stimulation is configured to modify the identified mental state in order to treat or improve a brain condition of the subject.

Figure 8:
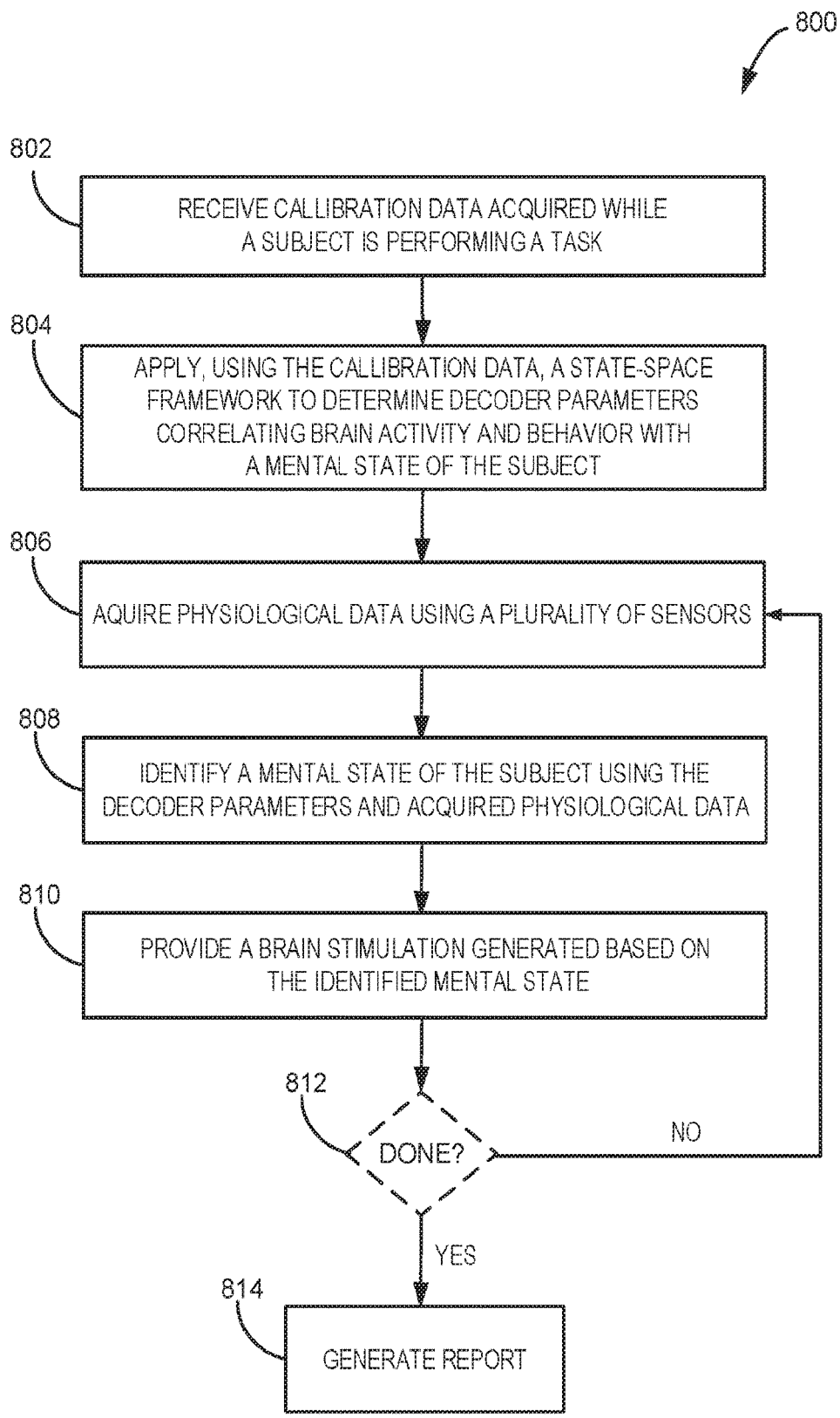
FIG. 8 is another flowchart setting forth steps of a process, in accordance with aspects of the present disclosure.

Referring now to FIG. 8, a flowchart setting forth steps of a process 800 for controlling a mental state of a subject, in accordance with aspects of the present disclosure, is shown. The process 800 may be carried out using a system as described with reference to FIG. 1, or any other suitable system, device or apparatus. Specifically, the process 800 may begin at process block 702 with receiving calibration data. As described, such calibration may include physiological and behavioral acquired using the plurality of sensors while the subject is performing a task. In some aspects, the data may be retrieved from a memory, database, server, or other data storage location. In other aspects, the data may be acquired at process block 802 using a system, as described. The acquired or received data may then be applied in a state-space framework, as described, to determine a plurality of decoder parameters correlating brain activity and behavior with a mental state of the subject, as indicated by process block 804. Example mental states may include a cognitive flexibility, learning states, and others.

Then at process block 806, physiological data may be acquired using the sensors. In particular, neural data indicative of brain activity may be acquired. Using the decoder parameters and the acquired physiological data, a mental state of the subject may then be identified, as indicated by process block 808. Then at process block 810, a brain stimulation generated based on the identified mental state may be provided. In some aspects, the brain stimulation may be determined based on a target mental state. Process blocks 806-810 may be repeated for a number of times, as determined by the conditional block 812. Upon termination, a report may be generated, as described. In some aspects, the brain stimulation provided at process block 810 may be adapted based on the identified mental state, either automatically or under the control of a clinician. In some implementations, the brain stimulation may sweep a voltage space and such that a response of the hidden state over a range of parameters is determined, effectively system-identifying a component of the KF transfer function B, as described, while treating the brain stimulation as one of the control inputs u. In some aspects, a linear feedback control (a damped proportional-integrative controller is likely sufficient) to command the mental state to desired values, or a target mental state, through adjustments of brain stimulation intensity.

Figure 9:
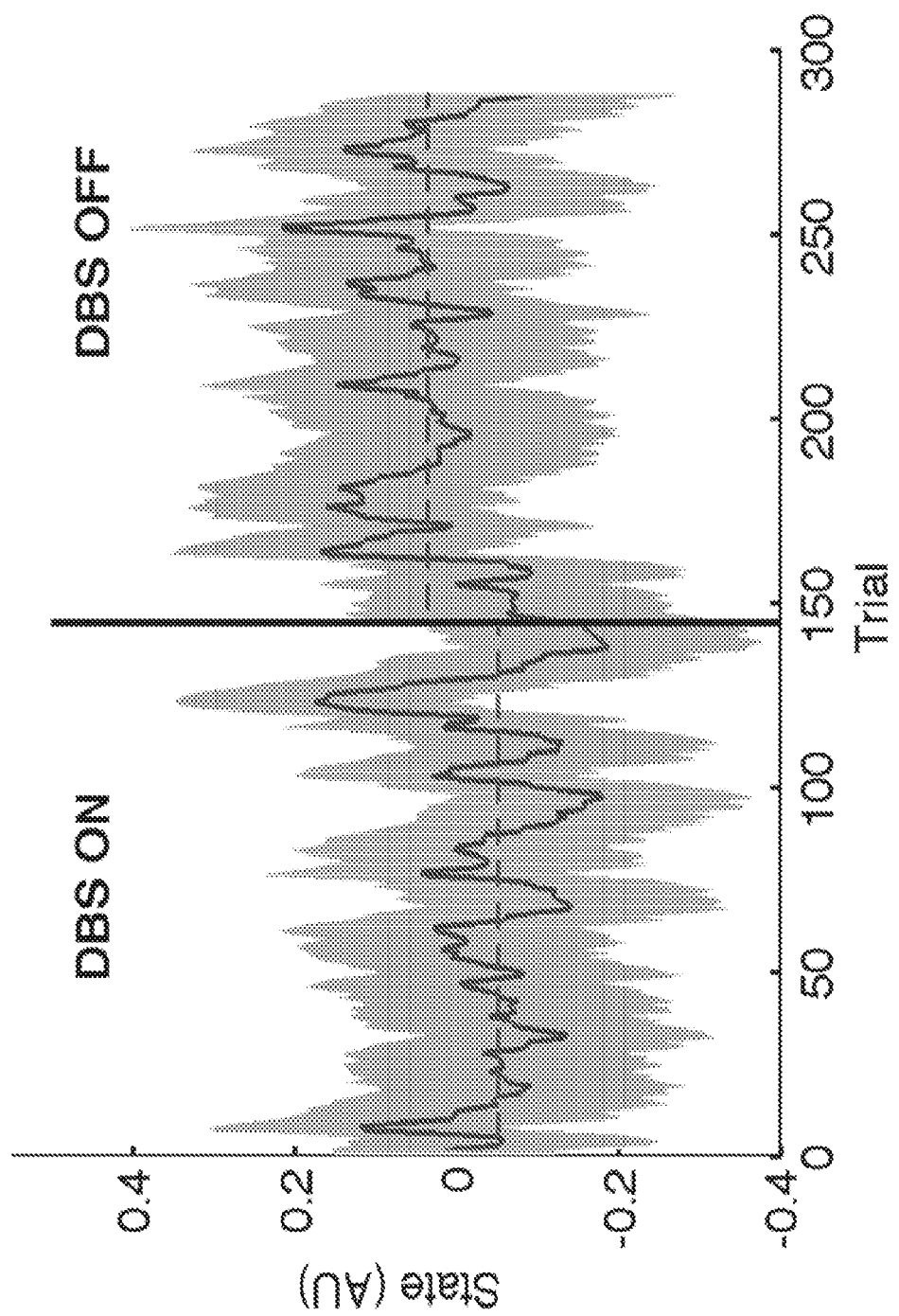
FIG. 9 is a graph showing an example of behavioral decoding applied to a psychiatric patient implanted with a deep brain stimulator while performing a MSIT, in accordance with aspects of the present disclosure.

By way of example, FIG. 9 shows a graph illustrating behavioral decoding applied to a psychiatric patient implanted with a deep brain stimulator (DBS) performing a MSIT. As appreciated from FIG. 9, when the DBS stimulation is off, a hidden mental state shifts to a higher value consistent with a prolonged response time. This demonstrates that it is possible to identify and control a hidden mental state, such as cognitive flexibility, by judicious selection of the stimulation.

In addition to descriptions above, specific examples are provided below, in accordance with the present disclosure. These examples are offered for illustrative purposes only, and are not intended to limit the scope of the present invention in any way. Indeed, various modifications in addition to those shown and described herein will become apparent to those skilled in the art from the foregoing description and the following example and fall within the scope of the appended claims.

EXAMPLE I

An important question in neuroscience is understanding the relationship between high-dimensional electrophysiological data and complex, dynamic behavioral data. One general strategy to address this problem is to define a low-dimensional representation of essential cognitive features describing this relationship. Here we describe a general state-space method to model and fit a low-dimensional cognitive state process that allows us to relate behavioral outcomes of various tasks to simultaneously recorded neural activity across multiple brain areas. In particular, we apply this model to data recorded in the lateral prefrontal cortex ("PFC") and caudate nucleus of non-human primates as they perform learning and adaptation in a rule-switching task. First, we define a model for a cognitive state process related to learning, and estimate the progression of this learning state through the experiments. Next, we formulate a point process generalized linear model to relate the spiking activity of each RFC and caudate neuron to the estimated learning state. Then, we compute the posterior densities of the cognitive state using a recursive Bayesian decoding algorithm. We demonstrate that accurate decoding of a learning state is possible with a simple point process model of population spiking. Our analyses also allow us to compare decoding accuracy across neural populations in the PFC and caudate nucleus.

Here we present one possible solution: a general state-space paradigm to model and fit a low-dimensional cognitive state process that allows us to relate outcomes of various behavioral tasks to simultaneously recorded neural activity across multiple brain areas. The paradigm consists of three steps. First, we estimate the dynamics of a cognitive state variable using previous knowledge of its influence on observed behavioral signals. Second, we construct models that use the estimated state and relevant covariates related to behavior to describe the statistical structure of neural activity. Last, we estimate the dynamic state again, this time using only the neural activity. We illustrate the proposed paradigm with an application to data recorded in the PFC and caudate nucleus of non-human primates as they perform learning and adaptation in a rule-switching task.

Cognitive State-Space Decoding Paradigm

Figure 10:
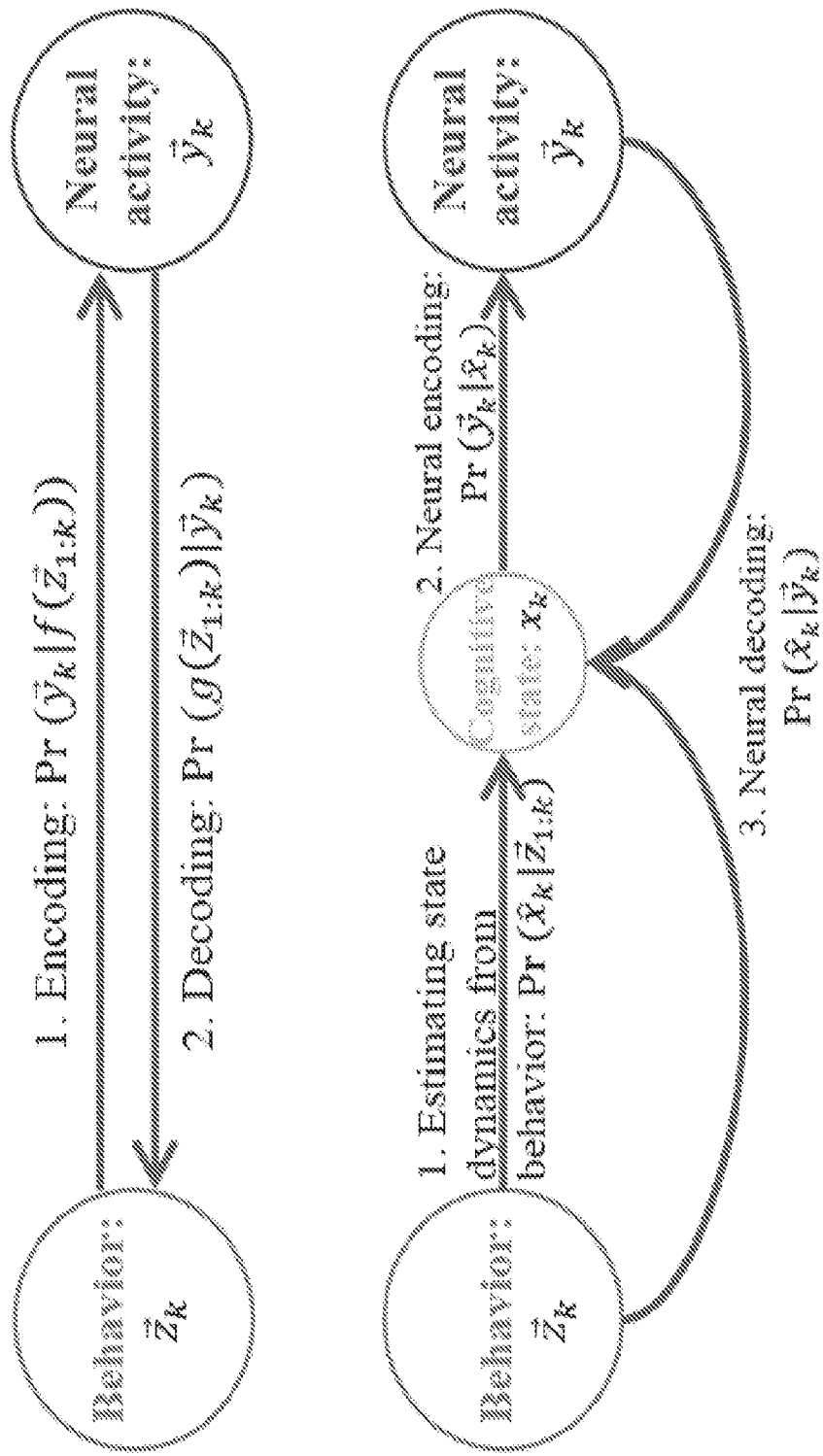
FIG. 10 is a schematic representation of the general three-model cognitive state-space paradigm, in accordance with aspects of the present disclosure, in comparison with traditional two-model approach.

In this section, we first construct a low-dimensional cognitive state process to relate behavior and neural activity. We then describe a general three-model paradigm to estimate the cognitive state in three steps, summarized in FIG. 10.

A. Model Framework

We model the underlying cognitive function (signal) during a task as a stochastic and dynamic process. The abstract state variable $x_k$ evolves through time according to some dynamics:

$$x_k | x_{k-1} \sim f(x_k | x_{k-1}) \tag{8}$$

In most situations, if not all, we do not observe the cognitive state. In other words, $x_k$ is "hidden". Some examples of this unobserved abstract cognitive state are reward motivation level, susceptibility to tear, flexibility of learning, etc.

Instead, we obtain some behavioral data $z_k$ related to the task, parameterized by $\theta_z$:

$$\vec{z}_k | x_k \sim g(\vec{z}_k | x_k; \theta_z) \tag{9}$$

$\vec{z}_k$ can be a vector with components from distinct distributions, both discrete and continuous. For example, $\vec{z}_k$ can includes a binary component of correct vs. incorrect choices and a continuous component of reaction times.

We also record, in addition to the behavioral data, some electrophysiological activity $\vec{y}_k$, parameterized by $\theta_y$:

$$\vec{y}_k | x_k \sim h(\vec{y}_k | x_k; \theta_y) \tag{10}$$

Similarly, $\vec{y}_k$ can also include both discrete neural signals such as single unit spiking activity and continuous neural signals such as local field potentials.

B. Estimating State Dynamics from Behavior

Our paradigm for estimating the cognitive state $x_k$ involves three steps. In the first step, we estimate the state dynamics, $p(x_k | \vec{z}_{1:k})$, using previous knowledge of the behavioral task structure $g(\vec{z}_z | x_k; \theta_z)$ and some smoothing constraints $f(x_k | x_{k-1})$ on the state process dynamics. Assuming the function g in (10) is known, we can use this known structure of g to estimate the state dynamics during behavioral experimental tasks:

$$p(x_k | \vec{z}_{1:k}) \propto p(\vec{z}_k | x_k) \int p(x_k | x_{k-1}) p(x_{k-1} | \vec{z}_{1:k-1}) dx_{k-1} \tag{11}$$

The integral on the right hand side of (12) is the one-step prediction density $p(x_{k-1}|\vec{z}_{1:k-1})$ defined by the Chapman-Kolmogorov equation. Here we have assumed that given the past state value, $x_{k-1}$, the distribution of the current state does not depend on the past behavior. The integral in Eqn. 11 typically cannot be solved analytically, but multiple numerical and approximation methods are available to compute its value at each time point. One approach is to apply some kind of filtering algorithm such as Kalman filters, which compute the distribution of the state given parameter estimates $\hat{\theta}$. Extensions of these methods, such as Expectation-Maximization (EM) and sequential Monte Carlo, simultaneously optimize the model parameter estimates and the unobserved cognitive state process.

C. Neural Encoding

Second, we characterize the relationship between the cognitive state and features of neural activity. In this encoding step, we use an estimate of $x_k$ from the previous step to identify models for function $h(\vec{y}|x_k; \theta_y)$ with unknown structures in Eqn. 10.

An example of $h(\vec{y}_k|x_k; \theta_y)$ can be a point process model with condition intensity function $\lambda(x_k)$, when yt is single unit neural spiking activity:

$$p(\vec{y}_k|x_k)=[\lambda(x_k;\theta_y)\Delta]^{\vec{y}_k}\exp[\lambda(x_k;\theta_y)\Delta] \quad (12)$$

where $\lambda(x_k; \theta_y)$ can be estimated by parametric models of generalized linear model form.

Another example of $\lambda(x_k; \theta_y)$ can be multivariate Gamma models with mean $\mu(x_k; \theta_y)$, when $\vec{y}_t$ is vector of power estimates in local field potential at specific frequencies.

In any case, we can treat the estimated state process from step 1 as known, with some uncertainty, and use model fitting methods, such as maximum likelihood to estimate the unknown model parameters.

D. Neural Decoding

Third, we estimate the dynamic state $x_k$ from a new dataset that includes both neural and behavioral activity. More specifically, in this "decoding" step, we compute the posterior distribution of the state process conditioned on the observed neural activity up until the current time:

$$p(x_k|\vec{y}_k,\vec{z}_k) \propto p(\vec{y}_k,\vec{z}_k|x_k)$$

$$\int p(x_k|x_{k-1})p(x_{k-1}|\vec{y}_{1:k-1},\vec{z}_{1:k-1})dx_{k-1} \quad (13)$$

If we assume that conditioning on the state, behavior and neural activity are independent, then $$p(\vec{y}_k,\vec{z}_k|x_k)=p(\vec{y}_k|x_k)p(\vec{z}_k|x_k) \quad (14)$$

If we choose to decode $x_k$ during the structured behavioral task, then we use both known g and identified models for h to estimate $x_k$. If we choose to decode $x_k$ outside of the structured task, we use identified h to estimate $x_k$.

Decoding Learning State from Spiking Activity

A. Experimental Data

We illustrate the application of the proposed paradigm with an example study. The behavioral and neural data are obtained from two monkeys performing a temporally delayed, on-line learning task in which they had to determine by trial-and-error which of four picture cues or spatial locations was currently rewarded within a learning block. Individual blocks followed either a "spatial" or an "object" rule. In the "spatial" rule, the animal was required to choose the target in the same location on every trial (e.g., always upper right). In the "object" rule, the correct action was to choose a picture that matched a picture cue (e.g., always a blue sailboat). The "spatial" rule is substantially easier and rewards perseverative behavior, while the "object" rule rewards flexibility.

In this specific example, the behavioral data is whether the monkey chose the correct location on each trial. The neural data is spiking activity recorded in the lateral prefrontal cortex (PFC) and caudate nucleus of the monkeys. The cognitive state is whether the subject has learned the rule of the task.

B. Estimate State Dynamics From Behavior

We take advantage of previous development of a dynamic approach to analyzing learning experiments with binary responses. We use a state-space model of learning in which a Bernoulli probability model describes behavioral task responses and a Gaussian state equation describes the hidden state process.

In other words, $p(\vec{z}_k|x_k)$ in Eqn. 13 can be expressed as the Bernoulli probability mass function:

$$p(\vec{z}_k|x_k)=q_k^{\vec{z}_k}(1-q_k)^{1-\vec{z}_k}, \quad (15)$$

where $q_k$ is defined by the logistic equation:

$$q_k = \frac{\exp(\mu + x_k)}{1 + \exp(\mu + x_k)}, \quad (16)$$

and $\mu$ is determined by the probability of a correct response by chance in the absence of learning or experience. Here $x_k$ defines the learning state of the animal at trial k in the experiment. The unobservable state process $x_k|x_{k-1}$ is defined as a random walk:

$$x_k=x_{k-1}+e_k, \quad (17)$$

where the $e_k$ are independent Gaussian random variables with mean 0 and variance $\sigma_e^2$. The one-step prediction density $p(x_k|\vec{z}_{1:k-1})$, or learning curve, is the probability of a correct response as a function of the state process and is calculated using an EM algorithm:

$$f(q|\mu, x_{k|k}, \sigma_{k|k}^2) = \quad (18)$$
$$[(2\pi\sigma_{k|k}^2)q(1-q)]^{-1}\exp\left(-\frac{1}{2\sigma_{k|k}^2}[\log[q(1-q)^{-1}\exp(\mu)]-x_{k|k}]^2\right)$$

Figure 11:
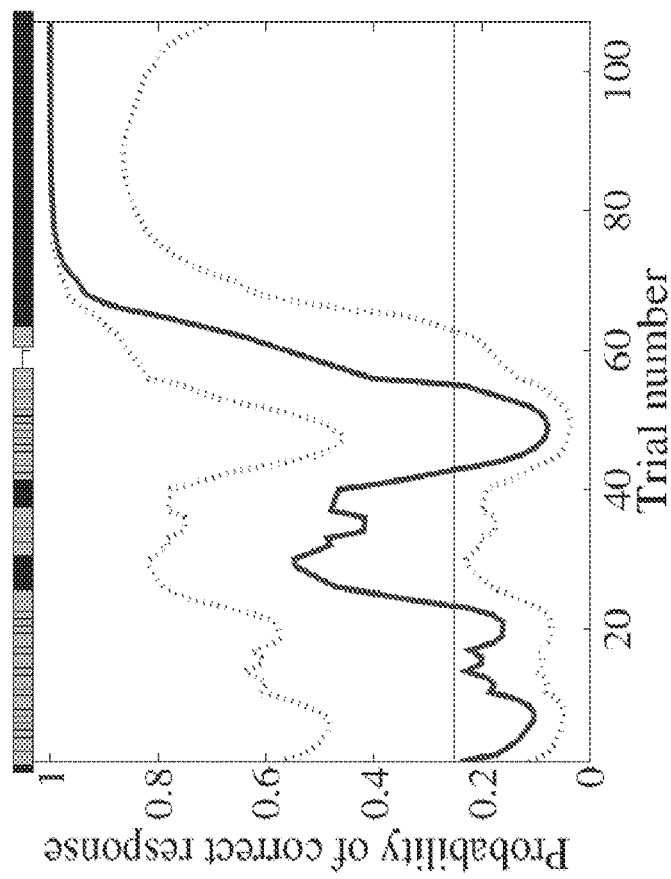
FIG. 11 are graphical examples of the learning curves estimated by an expectation minimization ("EM") algorithm following a state-space model, in accordance with aspects of the present disclosure.
Figure 11:
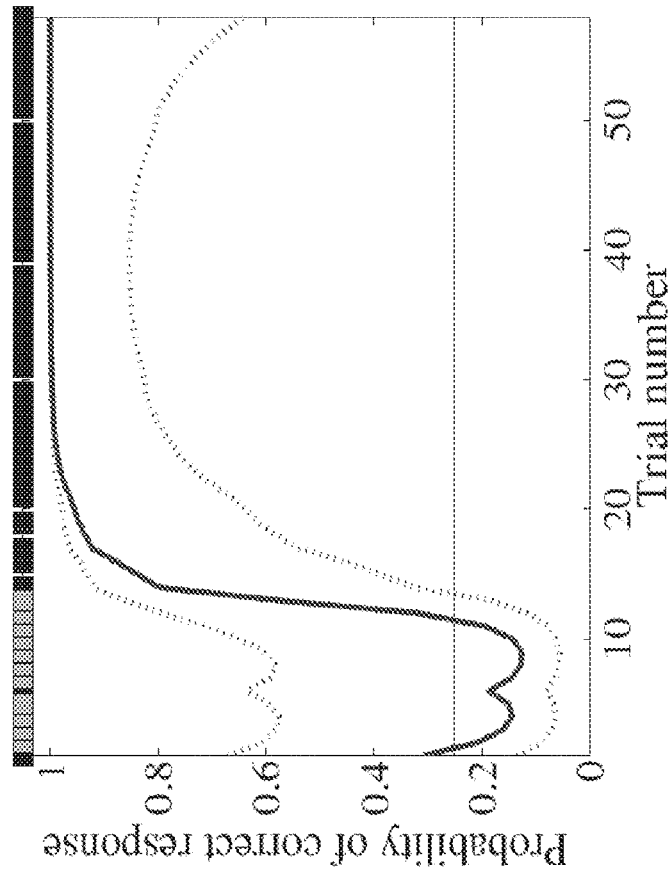

FIG. 11 shows two examples of the learning curves estimated by the EM algorithm in two learning blocks in the rule-switching behavioral task. The correct and incorrect responses are shown, respectively, by black and gray marks above the panels. Neglecting the possibility of behavioral preferences or other biases, the probability of a response occurring by chance is shown as a horizontal line at 0.25. Solid blue lines are the learning curve estimates, and the dotted blue lines are the associated 95% confidence intervals. The lower confidence bounds for the learning trial estimates remained above 0.25 after trial 14 and 63, which are, respectively the learning trials for the two learning block examples shown here.

For simplicity, we further dichotomize the trials within each learning block to be "learned" trials if the lower bound of the learning state estimate remains above 0.25 for the remainder for the trial block or "not learned" trials if otherwise.

C. Neural Encoding

Because the neural data in our example is spiking activity, we present a point process generalized linear model (GLM)

approach constructing a conditional intensity function that characterizes the spiking activity of PFC and caudate neurons. The conditional intensity function relates spiking probability simultaneously to the temporal features of the behavioral task.

In this case, the conditional intensity model is defined as follows:

$$\log \lambda^c(t) = \Sigma_{j=1}^{2} \Sigma_{i=1}^{N} \alpha_{i,j}{}^c B_{i,j}{}^c(t). \quad (19)$$

Here c=1, . . . , C is the index of the neuron. j=1, 2 is the binary indicator of the behavioral outcome of the trial, where j=1 and j=2 are "learned" and "not learned" states, respectively. $B_{i,j}{}^c(t)$ is a basis function for a cardinal spline for neuron c, trial type j. Cardinal splines are locally defined third-order polynomial functions that flexibly approximate arbitrary smooth functions using a small number of basis functions. Here, we use spline functions to capture the firing probability as a function of time relative to the picture cue. N is the number of spling control points used to fit the data. Here we chose N=16 control points. $\theta = [\{\alpha_{i,j}{}^c\}N_{i=1}]$ is a set of unknown parameters which relate the temporal features of the behavioral task to instantaneous spike rate. It follows from the definition of the conditional intensity function that the probability of a spike from neuron c in a small time interval [t, t+Δ) is approximately:

$$Pr(\text{Spike from neuron } c \text{ in } [t, t+\Delta) | \theta) \approx \lambda^c(t|\theta) \Delta \quad (20)$$

This spiking intensity function describes a GLM for the spike train data. Such GLMs have a number of nice properties, including convexity of the likelihood surface and asymptotic normality of the parameter estimates, which allow us to compute maximum likelihood estimates for the model parameters in a straightforward manner. We fit these GLMs using the estimated learning state from the behavioral data. We examine the model fits to the data from 500 ms before picture cue to 2500 ms after picture cue.

Figure 12:
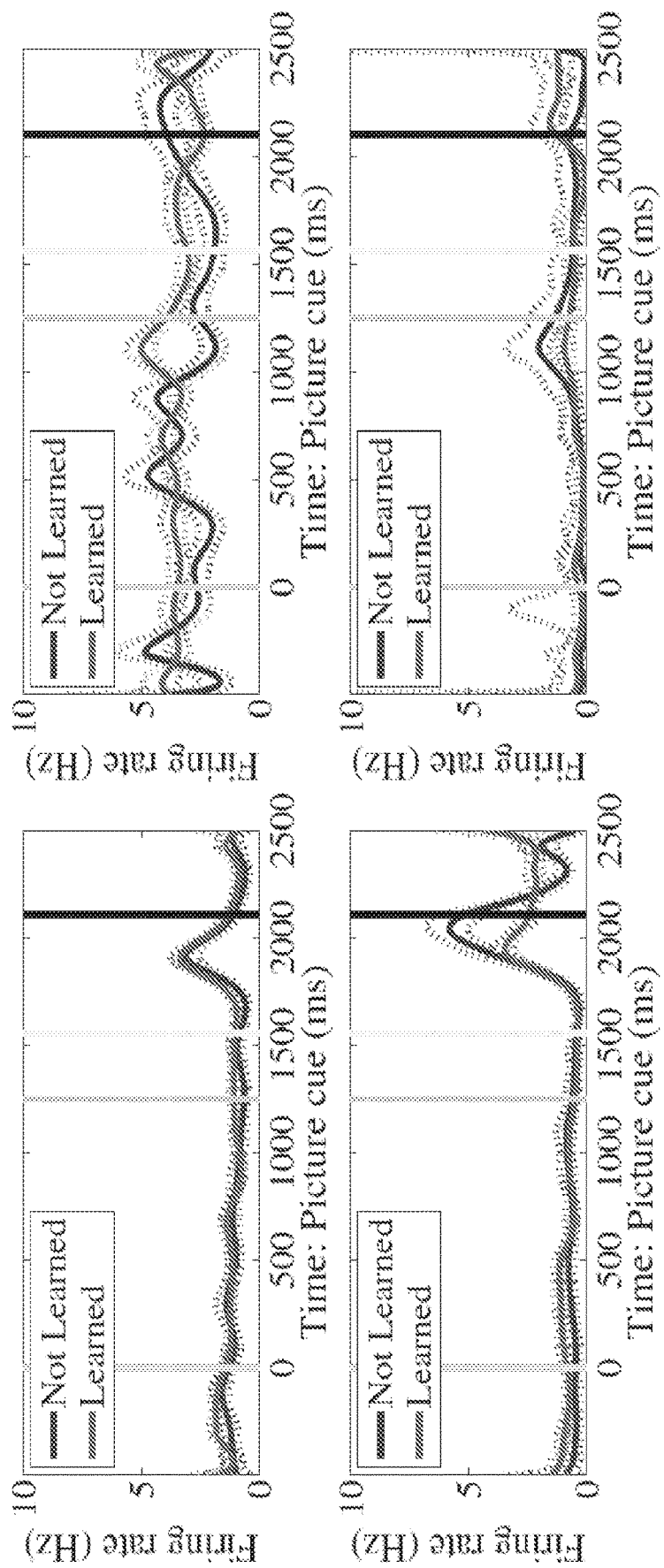
FIG. 12 are graphical examples showing model parameters and their uncertainty for a maximum likelihood fit to spiking data from four example neurons, in accordance with aspects of the present disclosure.

By way of example, FIG. 12 shows the model parameters and their uncertainty for the maximum likelihood fit to four example neurons in this spiking data. Each panel shows the spline estimates, in solid lines, and 95% confidence bounds in dashed lines, as a function of time relative to picture cue, represented by the vertical line in cyan. The times of go cue, feedback, and start of inter-trial interval are identified as vertical lines in green, yellow and black, respectively. The estimated intensity and 95% confidence bounds for the learned state and not-learned state are plotted in red and blue, respectively.

Top two and the lower-left panels in FIG. 12 show the model fit for three neurons in the caudate nucleus. For the neuron plotted in the top-left, at around 1000 ms after the picture cue and right before the go cue, the estimated intensity for learned trials in red is significantly higher than the estimated intensity for not-learned trials in blue. For the neuron plotted in the top-right, at around 2000 ms after the picture cue and within a 300 ins lag of the feedback, the estimated intensity for not-learned trials is significantly higher than that of the learned trials. For the neuron plotted in the lower-left, at around 800 ms after the picture cue, the estimated intensity for not-learned trials is significantly higher than that of the learned trials.

The lower-right panel in FIG. 12 shows the model fit for a neuron in the PFC. The 95% confidence bounds for the learned and not-learned trials are always overlapping, which means that the temporal spiking properties during the observation interval are not significantly different for the two learning states.

Figure 13B:
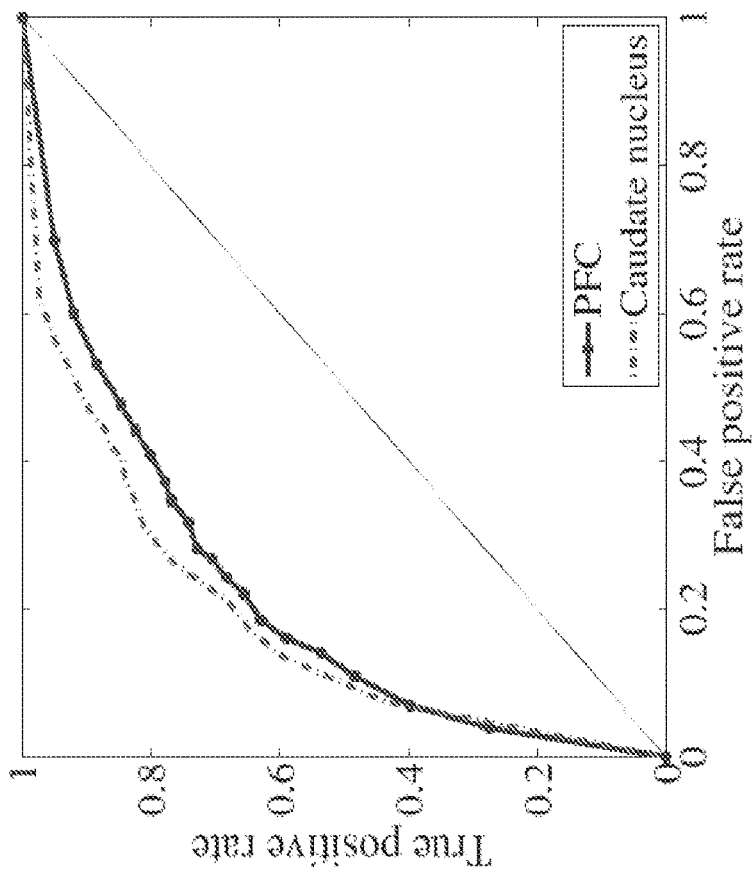
FIG. 13B is a graphical example of an receiver-operating characteristic ("ROC") curve for a state-space neural decoder applied to the learning process, in accordance with aspects of the present disclosure.
Figure 13A:
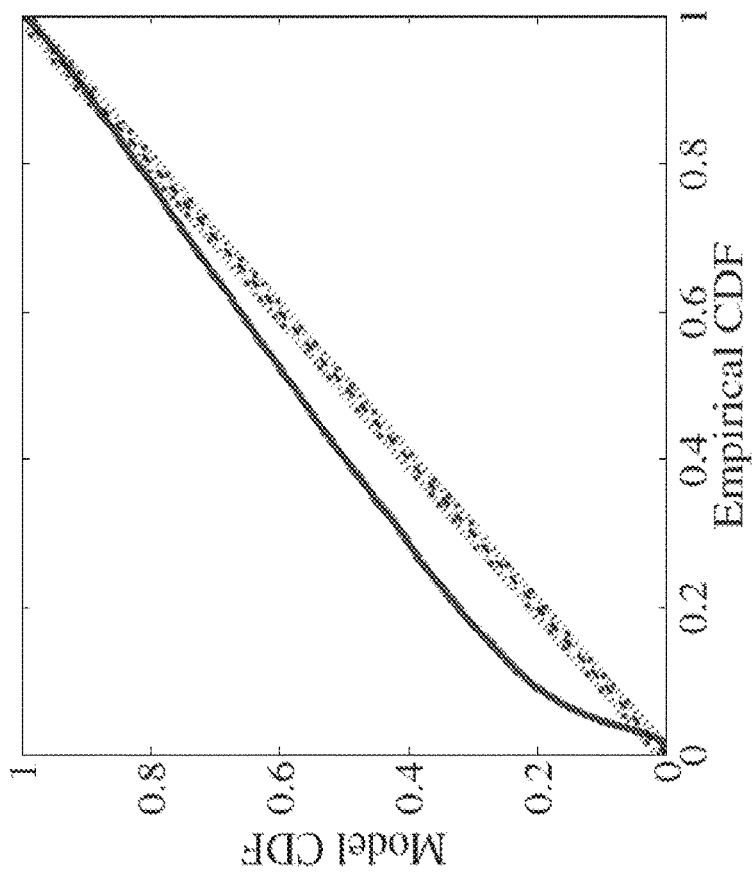
FIG. 13A is a graphical evaluation of a model fit through a Kolmogorov-Smirnov plot, in accordance with aspects of the present disclosure.

To assess the goodness-of-fit of the two-state model, we constructed Kolmogorov-Smirnov (K-S) plots of time-rescaled inter-spike intervals (ISIs). The time-resealing theorem produces a set of rescaled ISIs that are independent with an exponential distribution with mean 1 if the proposed model accurately describes the structure in the observed spiking activity. To construct the KS plot, we plot the empirical cumulative distribution of the rescaled ISIs against the theoretical cumulative distribution of the Exponential (1) distribution. The better the quality of the model fit, the closer the K-S plot should be to a 45 degree line. FIG. 13A shows an example K-S plot for the model fit. The model and empirical CDFs demonstrate a good overall fit, the curve being generally close to the identity line, demonstrating the model's ability to accurately reproduce and characterize the neural signal. Some evidence of misfit in the smaller rescaled ISIs may suggest some model misfit related to our assumptions of a dichotomized cognitive state and a lack of spiking history dependence structure in the point process model. More accurate modeling would likely lead to improvements in the overall goodness-of-fit and the resulting decoded state estimates.

D. Neural Decoding

The previous subsection focused on the construction of neural spiking models, which uses relevant covariates related to behavior to describe the statistical structure of neural spiking activity. In this subsection we present a simple recursive Bayesian algorithm to decode the dynamic state from the spiking activity. For each trial k, we compute the posterior distribution of the monkey's learning state given the combined spiking activity of the neural ensemble within the observation interval, [0,1];

$$p(\vec{y}_k | \Delta N_{1:T}) \propto p(\Delta N_{1:T} | \vec{x}_k) p(\vec{x}_k). \quad (21)$$

Here $p(\vec{x}_k)$ is the prior distribution of the state. In this case, we choose a uniform prior for the binary state. The observation model, or likelihood, is given by $$p(\Delta N_{1:T} | \vec{x}_k) \propto \Pi_{t=1}^{T} \Pi_{c=1}^{C} [\lambda^c(\vec{x}_k) \Delta]^{\Delta N_t}$$
$$\exp(-\lambda^C(\vec{x}_k) \Delta). \quad (22)$$

We perform a classification procedure by thresholding the posterior of the state at various cut-off probabilities to determine whether the monkey is in a "learned" or a "not learned" state during a particular trial. FIG. 13B shows the receiver-operating characteristic (ROC) curves, plotting the sensitivity of the cut-off, the probability of rejecting the null hypothesis when it is false, versus significance level, the probability of rejecting a null hypothesis when it is true. ROC curves using decoding results from the neural ensemble in PFC and caudate are plotted as a solid blue line and a dashed red line, respectively. The ROC curve based on spiking activity in the caudate is consistently above the ROC curve based on spiking activity in PFC, demonstrating that neural activity in the caudate provides a better decoding of the learning state than PFC. This result corroborates previous findings in the literature that the caudate contributes more closely to learning. Thus, as appreciated from FIG. 13B, the present model can accurately recover a latent state variable (learning) from neuronal firing in the PFC or caudate nucleus.

Discussion

The classical two-model state-space paradigm has been successfully applied to relate behavior and neural activity directly in low-dimensional, directly observable data. However, when both the behavioral and neural data become high-dimensional and multi-faceted, this direct approach becomes computationally challenging. Here we proposed a new three-model paradigm to characterize the relationship between behavior and the neural activity. We first introduced a cognitive state process whose dynamics can be estimated from behavior. We then used the state and relevant covariates related to behavior to describe the neural activity. Lastly, we estimated the dynamic state from a combination of behavioral and neural data.

We illustrated our paradigm with a specific example of two monkeys performing a temporally delayed, on-line learning task. We demonstrated that accurate decoding of the learning state is possible with a simple point process model of population spiking. Our analyses also allowed us to compare decoding accuracy across neural population in the PFC and caudate nucleus.

Immediate extensions to the application of the paradigm shown here are under active development. First, more accurate statistical descriptions of the behavioral data hopefully will lead to a more accurately estimated learning curve. Second, instead of working with the simplified, dichotomized learning state process, the neural encoding and decoding steps can deal directly with a continuous state process. Last, to improve the quality of fit, the point process models used for neural encoding can be expanded to include spiking history.

One goal of the proposed paradigm is to demonstrate the existence of meaningful relationships between complex behavior and high-dimensional neural activity. We achieve dimensionality-reduction by using the hidden cognitive state process to represent the relationship. Furthermore, by assigning some cognitive meaning to the hidden state, we can design experiments to determine the effect of manipulations of neural activity on cognitive influences of behavior. For the specific example shown here, the cognitive state can be thought of as a measure of learning flexibility, and we can modulate it to facilitate learning in the monkeys.

We envision the present paradigm to play a fixture role in the development of new types of closed-loop experiments, aiming to characterize causal relationships between neural activity and the behavior they encode. The proposed algorithm can allow investigators to identify and manipulate a low-dimensional correlate of cognitive influence in a content-specific way, altering neural activity related to certain cognitive features to modulate behavior. This may be an important step in treating mental diseases such as post-traumatic stress disorder and obsessive-compulsive disorders clinically.

EXAMPLE II

Behavioral tests are widely used to quantify features of cognitive processing. For a large class of behavioral signals, the observed variables are non-Gaussian and dynamic; classical estimation algorithms are ill-suited to modeling such data. In this research, we propose a mathematical framework to predict a cognitive state variable related to behavioral signals, which are best modeled using a Gamma distribution. The proposed algorithm combines a Gamma Smoother and EM algorithm in the prediction process. The algorithm is applied to reaction time recorded from subjects performing a Multi-Source Interference Task (MSIT) to dynamically quantify their cognitive flexibility through the course of the experiment.

Specifically, we have derived a complete state prediction algorithm for the class of linear state equations with Gamma distributed observations. The algorithm is based on maximum likelihood estimation using an approximate expectation-maximization (EM) algorithm; it sequentially estimates the model parameters and an unobserved cognitive state to maximize the likelihood of the observed data.

For the state estimation step, a Gamma process filter analogous to the Kalman filter for Gaussian observations is derived. This state space framework with a Gamma observation model is well-suited to a large class of behavioral and neural data, and the prediction algorithm derives an adaptive filter solution for this class of data. We discuss the result of this new filter on RT data recorded during a multi-source interference task (MSIT). The algorithm is applied to the dataset to predict cognitive flexibility of subjects through the course of an experiment.

Dynamic Model of Gamma Distributed Data

We assume that the cognitive state evolves according to a simple linear state equation; the equation describes the temporal evolution of the cognitive state from one trial to the next through the course of an experiment. The observed reaction time data is modeled by a Gamma distribution, and its statistics are linked to a function of the cognitive state. The Observed data is a sequence of continuous responses, and it is assumed that there are K trials for each experiment.

The cognitive state equation is modeled by a first order autoregressive process $$\chi_{K+1} = \alpha_1 * \chi_K + \alpha_0 + \varepsilon_K \chi_{K+1} = \alpha_1 * \chi_K + \alpha_0 + \varepsilon_K$$

where $(\alpha_0, \alpha_1)$ are model free parameters, $\varepsilon_K$ are independent zero mean Gaussian random variable with variance $\sigma_\varepsilon^2$. Parameter $0 \leq \alpha_1 < 1$ is the forgetting factor, and $\alpha_0/(1-\alpha_1)$ determines the steady-state value of the cognitive state.

The observed data is modeled by a Gamma distribution with an offset-term, the observation model is $$z_K = y_K + \alpha \quad \alpha \geq 0 \qquad (23.a)$$

$$f_{y_K|x_K}(y) \sim \frac{1}{\Gamma(v)} * \left(\frac{v*y}{\mu_K}\right)^v * \frac{1}{y} * e^{\frac{v*y}{\mu_K}} \qquad (23.b)$$

$$\mu_K = e^{b_1 * x_K + b_0} \qquad (23.c)$$

where $z_K$ are the observed data, the $\alpha$ is the offset-term and $y_K$ are samples of the Gamma distribution. The $\mu_K$ is the mean of Gamma distribution at k-th trial, and it is linked to the cognitive state by a log function. The log link function is a common link for the Gamma distributed data, but it can be replaced by any real-valued continuous function. The $(b_0,b_1)$ parameters determine how the cognitive state influences the distribution mean, and $1/v$ is the distribution dispersion. The $f_{y_K|x_K}(\cdot)$ relates the pdf of the Gamma distribution to $\mu_K$ and $v$.

The observed data and its underlying cognitive states are also dependent on the behavioral test features. The $(b_0,b_1)$ parameters, plus $(\alpha_0,\alpha_1)$, can be defined as a function of current and previous test features to reflect the dependence. For the MSIT task, we will describe the relationship between $(b_0,b_1)$ parameters and test/trial features.

The state prediction objective is to maximize the likelihood of the observed data given the test features. Because x is unobservable, and $\theta = (\alpha_0, \alpha_1, \sigma_\varepsilon^2, b_0, b_1, \alpha, v)$ is a set of unknown parameters, we utilize the EM algorithm for the state prediction. The EM algorithm is a well-established technique to perform maximum likelihood estimation when there is an unobserved process. Using the EM algorithm, the x process and $\theta$ parameter will be estimated to maximize the observed data likelihood. The EM algorithm has been used to estimate state-space models with point-process or binary observations; this new EM algorithm allows for state-space model estimation on Gamma observations. The algorithm can be extended to estimate state-space models with both binary and Gamma distributed observation data.

State Prediction Algorithm a. EM Algorithm, E-Step

The EM algorithm computes the maximum likelihood estimates of θ by maximizing the expectation of the complete data log-likelihood. The complete likelihood is the joint probability distribution of $X\{\chi_1, \ldots, \chi_K\}$ and $Y\{y_1, \ldots, y_K\}$ given θ, which for the proposed model is $p(X,Y|\theta,\chi_0) = f_{x_0}(\chi_0) \times$ $$\prod_{k=1}^{K} (2\pi\sigma_\varepsilon^2)^{-\frac{1}{2}} * \exp\{-(2\sigma_\varepsilon^2)^{-1}(\chi_k - \alpha_0 - \alpha_1 * \chi_{k-1})^2\} \times \quad (24)$$

$$\prod_{k=1}^{K} \frac{1}{\Gamma(\nu)} * \left\{ \left(\frac{\nu * y_k}{\mu_k}\right)^\nu * \frac{1}{y_k} * e^{-\frac{\nu * y_k}{\mu_k}} \right\}_{\mu_k = e^{b_1 * \chi_k + b_0}}$$

The first term on the right side of Eq. 24 defines the probability density of $x_0$, the initial value of state-space variable. Here, we assume that $x_0$ is a known value, though this can be replaced by any distribution and estimated as a part of EM procedure. The second term is defined by a Gaussian probability distribution for the state model in equation (1), and the third term is the Gamma distribution defined in Eqn. (23.c), iteration (l+1) of the E-step, we compute the expectation of the complete data log likelihood given the Y and the parameter estimate from iteration, $l, \theta^{(l)} = (\alpha_0^{(l)}, \alpha_1^{(l)}, \sigma_\varepsilon^{2(l)}, b_0^{(l)} b_1^{(l)}, \alpha^{(l)}, \nu^{(l)}, \chi_0^{(l)})$, which is defined as $$E[\log(p(X, Y | \theta)) || Y, \theta^{(l)}] = \quad (25)$$

$$E\left[K\left(\log\frac{\nu^\nu}{\Gamma(\nu)}\right) + (\nu - 1)\sum_{k=1}^{K} \log y_k - \nu \sum_{k=1}^{K} \left(\log\mu_k + \frac{y_k}{\mu_k}\right) || Y, \theta^{(l)}\right] +$$

$$E\left[-\frac{K}{2}\log(2\pi\sigma_\varepsilon^2) - (2\sigma_\varepsilon^2)^{-1}\sum_{k=1}^{K} (\chi_k - \alpha_0 - \alpha_1\chi_{k-1})^2 || Y, \theta^{(l)}\right]$$

To evaluate the E-step, we have to calculate the following terms for $k = 1, \ldots, K$ $$\chi_{K|K} = E[\chi_K || Y, \theta^{(l)}] \quad (26.a)$$

$$W_{K|K} = E[\chi_K^2 || Y, \theta^{(l)}] \quad (26.b)$$

$$W_{K,K-1|K} = E[\chi_K \chi_{K-1} || Y, \theta^{(l)}] \quad (26.c)$$

$$M_{K|K}(t) = E[\exp(t\chi_K) || Y, \theta^{(l)}] t \in R \quad (26.d)$$

The notation K|k denotes the fixed interval smoothing, it is the expectation of state variable, or a function of the state variable, at k given the whole observation up to step K. To compute these expectations, a previous strategy for linear Gaussian state and observation models is utilized. The strategy is decomposed into four steps: a recursive filtering algorithm to compute K|k, a fixed interval smoothing algorithm to calculate $\chi_{K|K}$ and $\sigma_{K|K}^2$, a state-space covariance algorithm to estimate $W_{K|K}$, $W_{K,K-1|K}$ and a moment generating function to compute $M_{K|K}(t)$.

b. Filter Algorithm

Given $\theta^{(l)}$, the one-step prediction of mean and variance of the state space variable is $$\chi_{k|k-1} = \alpha_1^{(l)} \chi_{k-1|k-1} + \alpha_0^{(l)} \quad (27.a)$$

$$\sigma_{k|k-1}^2 = \alpha_1^{(l)2} \sigma_{k-1|k-1}^2 + \sigma_\varepsilon^{2(l)} \quad (27.b)$$

The definitions for the mean and variance of the state space variable are sufficient to compute the Gaussian one-step prediction probability density. To compute the $\chi_{k|k}$, we write the posterior probability density of the state variable given the observed data and $\theta^{(l)}$, and we use a Gaussian approximation.

$$p(\chi_k | \theta^{(l)}, y_{1 \ldots k}) \propto p(y_k | \theta^{(l)}, \chi_k) \times (\chi_k | \theta^{(l)}, y_{1 \ldots k-1}) \propto \quad (28)$$

$$\frac{1}{\Gamma(\nu^{(l)})} \left(\frac{\nu^{(l)} * y_k}{\mu_k^{(l)}}\right)^{\nu^{(l)}} \frac{1}{y_k} e^{-\frac{\nu^{(l)} y_k}{\mu_k^{(l)}}} \times (2\pi\sigma_{k|k-1}^2)^{-\frac{1}{2}}$$

$$\exp\{-(2\pi\sigma_{k|k-1}^2)^{-1}(\chi_k - \alpha_0^{(l)} - \alpha_1^{(l)} \chi_{k-1|k-1})^2\} \propto$$

$$(2\pi\sigma_{k|k}^2)^{-\frac{1}{2}} \exp\{-(2\pi\sigma_{k|k}^2)^{-1}(\chi_k - \alpha_0^{(l)} - \alpha_1^{(l)} \chi_{k|k})^2\}$$

The last line in Eqn. 28 is the Gaussian approximation of the posterior probability with parameters $\chi_{k|k}$ and $\sigma_{k|k}^2$ still to be determined. For a Gaussian distribution, the maximum of the pdf, and similarly the log of pdf, happens at its mean value. The mean of the Gaussian approximation is the point defined as $$\left. \frac{\delta \log p(\chi_k | \theta^{(l)}, y_{1 \ldots k})}{\delta \chi_k} \right|_{\chi_{k|k}} = 0 \quad (29.a)$$

$$\chi_{k|k} = \chi_{k|k-1} + \sigma_{k|k-1}^2 * \nu * \left[ -\frac{\partial \log \mu_k}{\partial \chi_k}\left(1 - \frac{y_k}{\mu_k}\right) \right]_{\chi_{k|k}} \quad (29.b)$$

The variance term is defined by the second derivative of the distribution log, which is $$\left. \frac{\delta \log p(\chi_k | \theta^{(l)}, y_{1 \ldots k})}{\delta \chi_k^2} \right|_{\chi_{k|k}} = -\sigma_{k|k}^{2-1} \quad (30.a)$$

$$\chi_{k|k}^{2-1} = \sigma_{k|k-1}^{2-1} + \nu\left(\left(1 - \frac{y_k}{\mu_k}\right)\frac{\partial^2 \log \mu_k}{\partial \chi_k^2} + \left(\frac{\partial^2 \log \mu_k}{\partial \chi_k}\right)^2 \frac{y_k}{\mu_k}\right)\bigg|_{\chi_{k|k}} \quad (30.b)$$

The $\chi_{k|k}$ computation normally requires multiple iterations of Eqn. 29. However, this can be avoided with the Gaussian approximation technique used previously. The technique starts by taking the log of the posterior density and taking its derivative with respect to $$\sigma_{k|k}^{2-1}(\chi_k - \chi_{k|k}) \propto \sigma_{k|k-1}^{2-1}(\chi_k - \chi_{k|k-1}) + \frac{\partial \log \mu_k}{\partial \chi_k} \nu\left(1 - \frac{y_k}{\mu_k}\right) \quad (31)$$

Assuming the Gaussian estimate is valid, the relationship should be approximately true for all the values of $x_k$. Evaluating at $x_k = x_{k|k}$ gives $$\chi_{k|k} = \chi_{k|k-1} + \sigma_{k|k}^2 * \nu * \left[ -\frac{\partial \log \mu_k}{\partial \chi_k} * \left(1 - \frac{y_k}{\mu_k}\right)\right]_{\chi_{k|k-1}} \quad (32)$$

Differentiating Eqn. 31 again, and replacing $x_\kappa = x_{k|k-1}$ gives the posterior variance equation:

$$\sigma_{K|K}^{2}{}^{-1} = \sigma_{K|K-1}^{2}{}^{-1} + v\left(\left(1 - \frac{y_K}{\mu_K}\right)\frac{\partial^2 \log \mu_K}{\partial \chi_k^2} + \left(\frac{\partial \log \mu_K}{\partial \chi}\right)^2 \frac{y_K}{\mu_K}\right)\Bigg|_{\chi_{K|K-1}} \quad (33)$$

c. Fixed Interval Smoother

Given the sequence of posterior one-step estimates, ($\chi_{K|K}$, $\sigma_{K|K}^2$), we use the fixed-interval smoothing algorithm to compute $\chi_{K|K}$ and $\sigma_{K|K}^2$. The smoothing algorithm is $$\chi_{K|K} = \chi_{K|K} + A_K(\chi_{K-1|K} - \chi_{K+1|K}) \quad (34.a)$$

$$A_K = \sigma_{K|K}^2 * \alpha_1^{(l)} * \sigma_{K+1|K}^{2-1} \quad (34.b)$$

$$\sigma_{K|K}^2 = \sigma_{K|K}^2 + A_K^{2*}(\sigma_{K+1|K}^2 - \sigma_{K+1|K}^2) \quad (34.c)$$

for k=K−1, ..., 1 and initial conditions $\chi_{K|K}$ and $\sigma_{K|K}^2$.

d. State-Space Covariance and Moment Generating Function

Given the Gaussian assumption for the posterior distribution of the hidden state, the expectation $M_{K|K}(t)$ for an arbitrary t is $$M_\chi(t) = \exp(t^*\chi_{K|K} + \frac{1}{2}*t^{2}*\sigma_{K|K}^2) \quad (35)$$

which is the MGF for a normal distribution with mean $\chi_{K|K}$ and variance $w_{K|K}$. The covariance term in equation (26.c) is given by $$\sigma_{K-1,K|K} = A_{K-1} * \sigma_{K|K}^2 \quad (36)$$

The variance and covariance terms for the E-step will be $$W_{K|K} = \sigma_{K|K}^2 + \chi_{K|K}^2 \quad (37.a)$$

$$W_{K-1,K|K} = \sigma_{K|K}^2 + \chi_{K-1|K} * \chi_{K|K} \quad (37.b)$$

e. EM Algorithm, M-Step

The model parameter θ is updated to maximize the observed maximum likelihood. The update rule for the observation model parameters, ($b_0, b_1, \alpha, v$), is $$\frac{\partial Q}{\partial v} \equiv \quad (38.a)$$

$$K\left(\log v + 1 - \frac{\Gamma'(v)}{\Gamma(v)}\right) + \sum_{k=1}^{K} \log(y_\kappa) - E(\log \mu_\kappa) - y_\kappa W(1/\mu_\kappa) = 0$$

$$\frac{\partial Q}{\partial b_0} \equiv \sum_{k=1}^{K} \frac{\partial E(\log \mu_\kappa)}{\partial b_0} + \sum_{k=1}^{K} y_\kappa * \frac{\partial E(1/\mu_\kappa)}{\partial b_0} = 0 \quad (38.b)$$

$$\frac{\partial Q}{\partial b_1} \equiv \sum_{k=1}^{K} \frac{\partial E(\log \mu_\kappa)}{\partial b_1} + \sum_{k=1}^{K} y_\kappa * \frac{\partial E(1/\mu_\kappa)}{\partial b_1} = 0 \quad (38.c)$$

$$\frac{\partial Q}{\partial \alpha} \equiv (1-v)\sum_{k=1}^{K} \frac{1}{y_\kappa} + v\sum_{k=1}^{K} W(1/\mu_\kappa) = 0 \quad (38.d)$$

The set of Eqns. 38 can be solved numerically to find the new set of observation model parameters. The expectation terms $E(\log \mu_\kappa)$ and $E(1/\mu_\kappa)$, are defined by $$E(\log \mu_\kappa) = E(b_1 * \chi_\kappa + b_0) = b_1 * \chi_{K|K} + b_0 \quad (39.a)$$

$$E(1/\mu_\kappa) = \exp(-b_0)E(\exp(-b_1 \chi_\kappa)) \quad (39.b)$$

To compute Eqn. (39.b), we use the MGF function already defined in Eqn. 25. The update rule for the state equation parameters, ($\alpha_0, \alpha_1, \sigma_\varepsilon^2, \chi_0$), is $$\begin{bmatrix} \alpha_0^{(l+1)} \\ \alpha_1^{(l+1)} \end{bmatrix} = \begin{bmatrix} K & \sum_{k=1}^{K} \chi_{K-1|K} \\ \sum_{k=1}^{K} \chi_{K-1|K} & \sum_{k=1}^{K} W_{K-1|K} \end{bmatrix}^{-1} * \begin{bmatrix} \sum_{k=1}^{K} \chi_{K|K} \\ \sum_{k=1}^{K} W_{K,K-1|K} \end{bmatrix} \quad (40.a)$$

$$\sigma_\varepsilon^{(l+1)2} = \frac{1}{K}\sum_{k=1}^{K} [W_{k|K} + \alpha_0^{(l+1)2} + \alpha_1^{(l+1)2}W_{k-1|K} \cdots - 2\alpha_0^{(l+1)}\chi_{k|K} - 2\alpha_1^{(l+1)}W_{k-1|K} + 2\alpha_1^{(l+1)}2\alpha_0^{(l+1)}\chi_{k-1|K}] \quad (40.b)$$

$$\chi_0^{(l+1)} = (\chi_{1|K} - \alpha_0^{(l+1)})/\alpha_1^{(l+1)} \quad (40.c)$$

the $\alpha_0\alpha_1$ parameters are updated first, and then $\sigma_\varepsilon^2, \chi_0$ parameters will be updated.

The complete state prediction algorithm is defined through equations 1 to 19. Table 1 describes the algorithm implementation steps. The algorithm terminates whenever the log-likelihood increment falls below a preset positive threshold, ε, log p(X, Y|θ$^{(l)}$)≤log p(X,Y|θ$^{l-1}$)+ε.

TABLE 1

State Prediction Algorithm Implementation

1. Initialize model parameters: θ$^{(0)}$
2. State-space filtering
3. State-space smoothing
4. Covariance and MGF computation
5. Parameter update
6. Iterate steps 2 to 5 till convergence Multi-Source Interference Task The MSIT, previously above, is designed to evoke a high level of cognitive conflict. It is a successor to a long line of cognitive conflict tasks, originating with the Stroop color-word conflict task. MSIT combines this with flanker and motor mapping effects to increase the cognitive load. Trials are classified as "non-interference" (easy, low load) or "interference" (hard, high load). In general, subjects rapidly acquire the task concept and are able to perform at nearly 100% correct. The key behavioral readout is their RT in response to a sequence of trials. First, on interference trials, patients respond 200-400 milliseconds more slowly on average than on non-interference trials. Second, when the effect of (non)interference is controlled for, an effect of trial sequencing emerges. If an interference trial is followed by another interference trial (I2I), the interference effect lessens on the second trial the brain adapts. Conversely, if an interference trial follows a non-interference trial (N2I), the effect of interference is much larger, because the brain acquires an easy-trial "response set" that is disrupted by the switch. This is often referred to as the "Grafton effect", The exact nature of the effect is debated, with some authors arguing it to be primarily driven by stimulus/response switches and others attributing it to competing mental processes. It nevertheless does occur, and interestingly, is dependent on the cingulate cortex—surgical ablation of the cingulate also eliminates the Gratton effect specifically in MSIT. Thus, we can use the effect of trial-type switches (after trial type itself is controlled for) as a marker for a subject's moment-to-moment cognitive flexibility. For the MSIT experiment, we model the RT, $z_\kappa$ in Eqn. 23, by $$b_0 = c_0 + c_1 I_i + c_2 Z_{K-1} \quad (41.a)$$

$$b_1 = I_{n2i} + c_3 I_{i2n} \quad (41.b)$$

where ($c_0$, $c_1$, $c_2$, $c_3$) are the model free parameters, and $I_i$ is an indicator function for the interference trials. The $I_{n2i}$ is the indicator function for the non-interference to interference trials, and the $I_{i2n}$ is the indicator function for the interference to non-interference trials. The state-space variable ($x_\kappa$) represents the influence of trial switching on RT, and it can be thought of as a measure of cognitive flexibility/rigidity.

State Prediction in a Sample Experiment

FIGS. 14-19 show a sample MSIT analysis on a human subject, plus the cognitive state prediction results. The initial values of the model parameters, ($c_0$, $c_1$, $c_2$, $c_3$, v) are computed using a GLM regression algorithm, assuming $\chi_\kappa=1$ and $\alpha=0$. For the state equation, $a_1$ set to 1 and $a_0$ is set to zero. The $\sigma_c^2$, the noise term in the state equation, is estimated by the EM algorithm.

Figure 14:
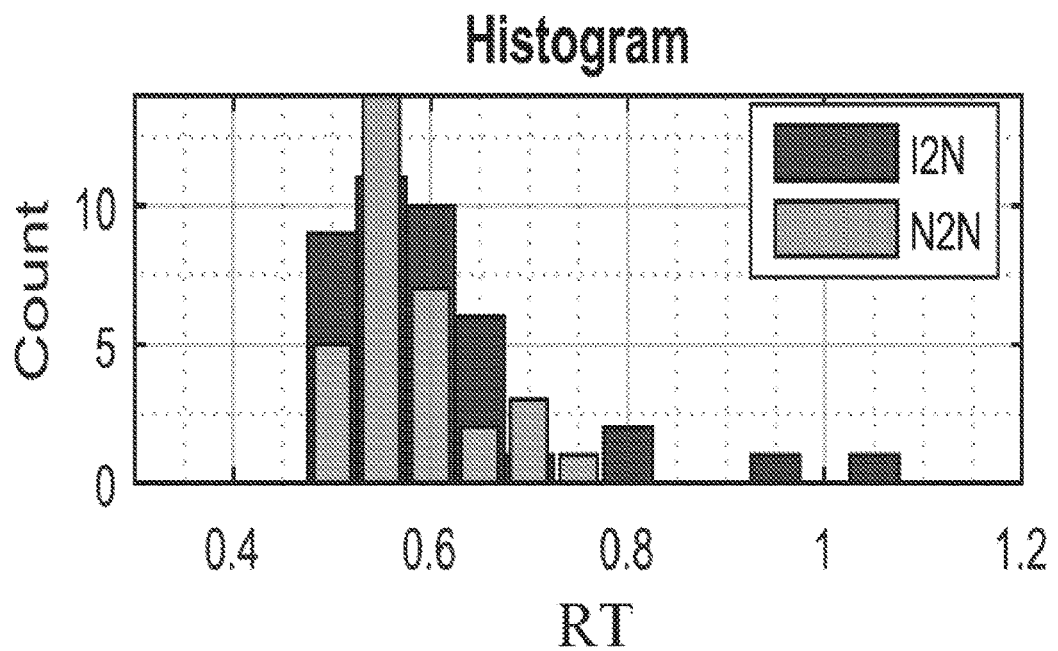
FIG. 14 are graphs showing reaction time histograms for different sequence trials.
Figure 14:
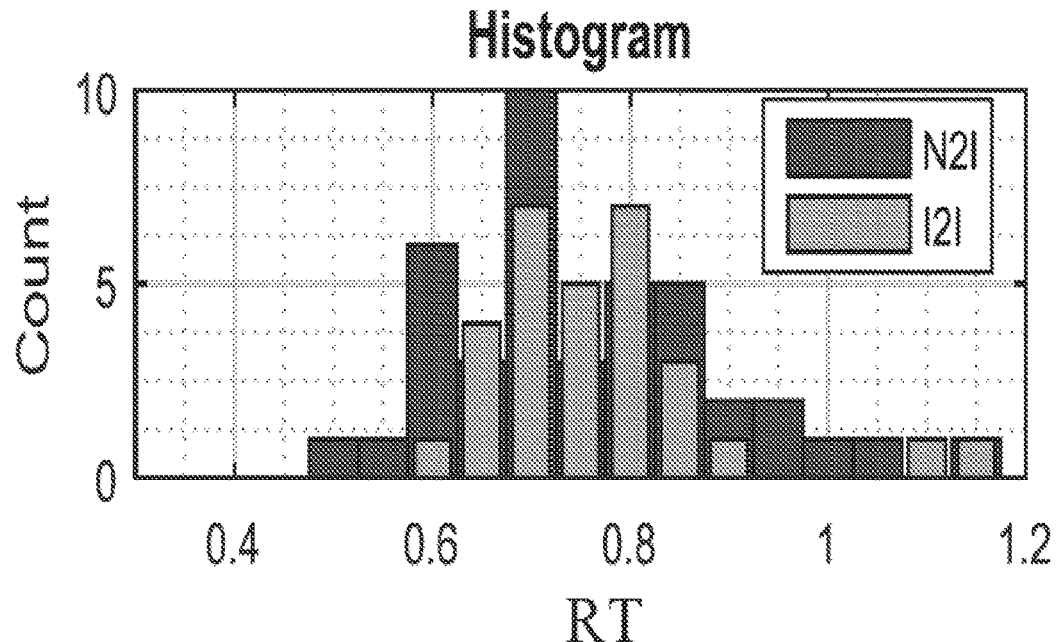

FIG. 14 shows the distribution of RT for two example runs of the MSIT. From the histograms we see that the RT interference effect is about 250 milliseconds, and the distribution is positively-skewed. Despite a similar RT distribution in non-interference-to-interference and interference-to-interference trials, their RTs change significantly through the experiment.

Figure 15:
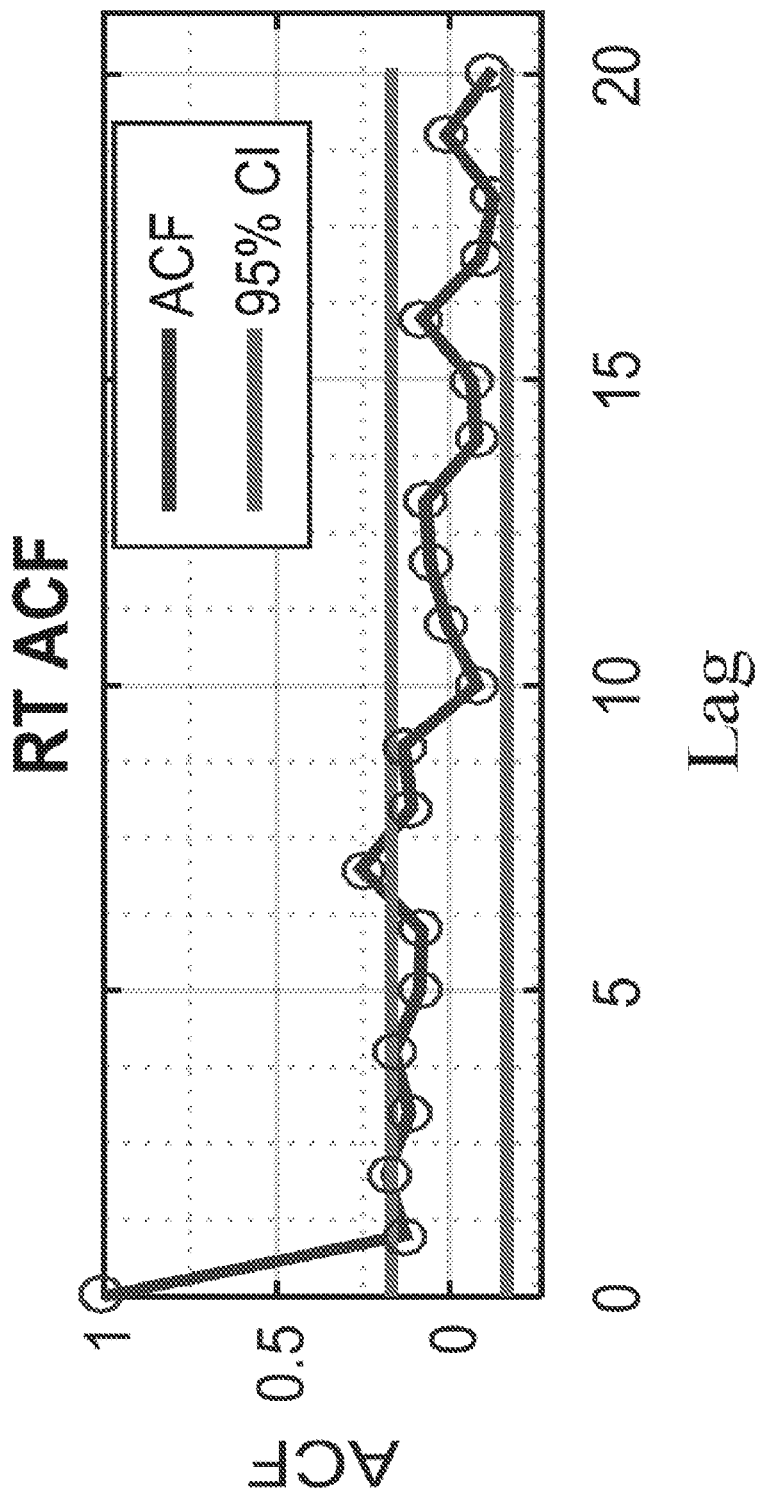
FIG. 15 is a graph illustrating an auto-correlational estimate for reaction time.

FIG. 15 shows the auto-correlation estimate for the RT. The graph result suggests the RTs are un-correlated, or weakly correlated, when not accounting for interference effect.

Figure 16:
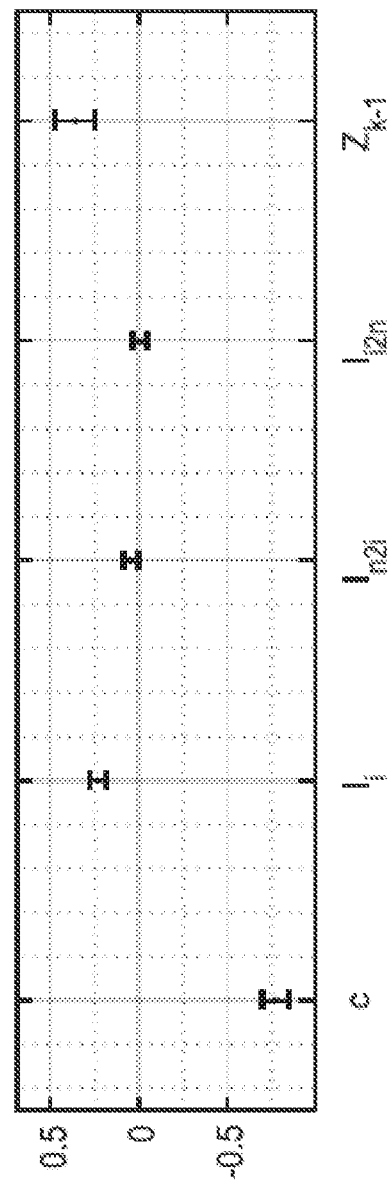
FIG. 16 is a graph showing an example generalized linear model ("GLM") regression estimate, in accordance with aspects of the present disclosure.

FIG. 16 shows the GLM regression estimate of the coefficients. The GLM regression algorithm estimates a positive coefficient for $Z_{\kappa-1}$, meaning that $Z_{\kappa-1}$ and $Z_\kappa$ are positively correlated when accounting for interference and switching effects. The auto-correlation analysis fails to extract existing correlation between $Z_\kappa$ and $Z_{\kappa-1}>0$. This may reflect a model mis-specification, but may also imply that the dependence between $Z_\kappa$ s is unobservable if we exclude ($I_i I_{i2n} I_{n2i}$) terms. The $I_i$ term defines the interference effect; the GLM estimate for the $I_i$ coefficient is 0.25 meaning that interference trials take approximately 28% ($\mu_\kappa$ definition in Eqn. (21.c), exp(0.25)≈1.28 longer than non-interference trials ignoring other terms of the model. The GLM estimate for the $I_{i2n}$ coefficient is a positive value, supporting the possibility of observing an overall Gratton effect on non-interference to interference trials. The GLM estimate for the $I_{i2n}$ coefficient is close to zero, suggesting non or minuscule Gratton effect on $I_{i2n}$ trials of the experiment. For the dynamic model defined in Eqn. (20), the $I_{i2n}$ coefficient is equal to 1; the $x_0$ (initial value of the $x_\kappa$) is assumed to be equal to the $I_{i2n}$ coefficient derived by the GLM regression estimate. The $c_3$ in equation (20.b) is the GLM estimate of the $I_{i2n}$ coefficient normalized by the $I_{i2n}$ coefficient estimate. Equations (2.c) and (20) define the relationship between the mean of RT and $x_\kappa$, cognitive flexibility/rigidity. The mean is an increasing function of $x_\kappa$; it means that the RT increment on the switching trials is linked to higher values of $x_\kappa$, which is interpreted as cognitive rigidity. Conversely, the cognitive flexibility can be interpreted as the RT reduction, which corresponds to smaller or negative $x_\kappa$ s.

Figure 17:
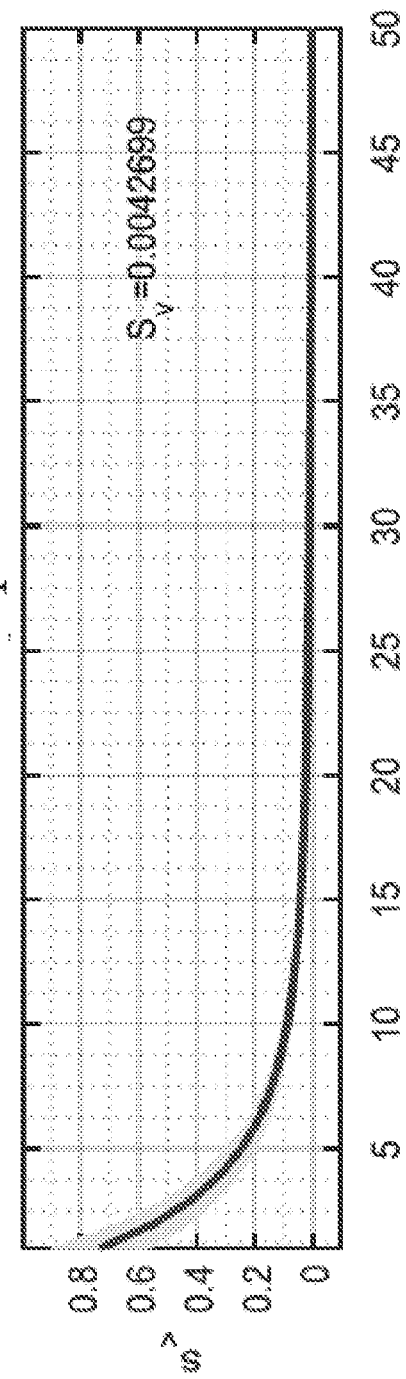
FIG. 17 is a graph showing results from a successive EM algorithm, in accordance with aspects of the present disclosure.

FIG. 17 shows the $\sigma_\varepsilon^2$ estimate through a successive EM algorithm. The EM estimate of $\sigma_\varepsilon^2$, significantly drops from its initial guess and converges to 0.004. This low variance estimate matches with a narrower confidence interval, or simply a more precise estimate, of $\chi_{K|K}$. The EM estimate can be applied to predict any other free parameters of the RT model.

Figure 18:
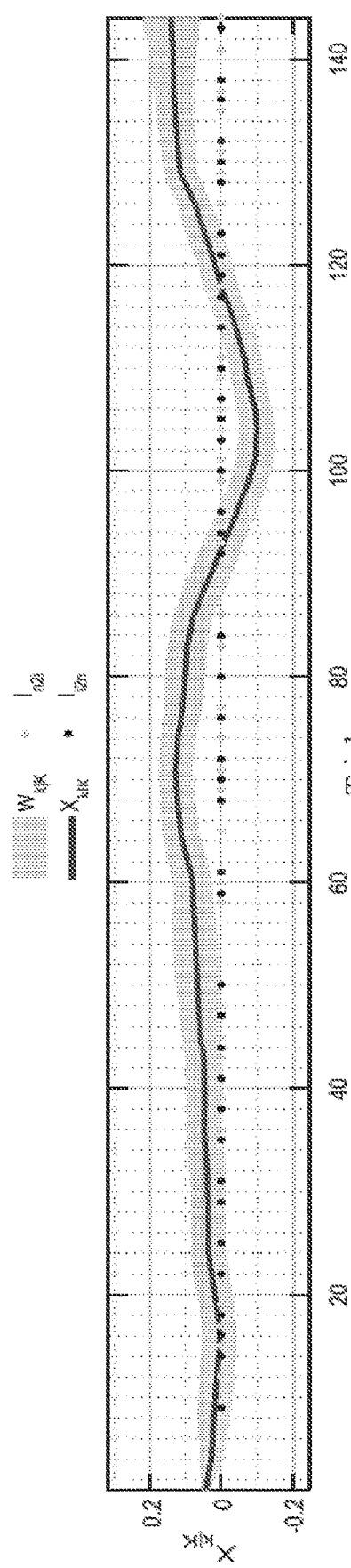
FIG. 18 is a graph demonstrating that a cognitive flexibility state can be estimated on a trial-to-trial basis from a patient's behavior on an MSIT task, in accordance with aspects of the present disclosure.

FIG. 18 shows $\chi_{K|K}$, the cognitive flexibility/rigidity prediction. The $\chi_{K|K}$ graph shows how RT on switching trials changes in the time course of the experiment. There is about a 15% increment in the RT of a trial switch in the midst of the experiment, it then drops about 15% and increases again at the end of the experiment.

Figure 19:
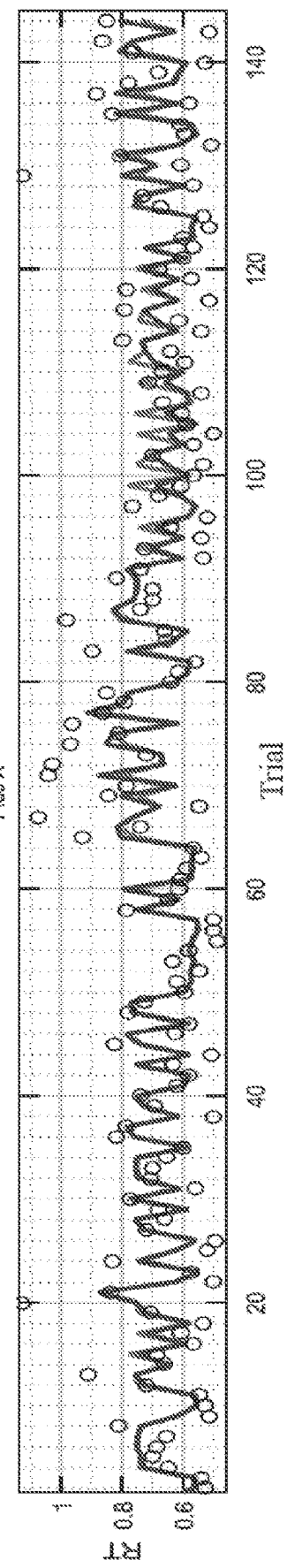
FIG. 19 is a graph showing observed reaction time versus trial number, in accordance with aspects of the present disclosure.

FIG. 19 shows observed WI plus its prediction with and without the cognitive state ($x_k$). The result supports the hypothesis of a dynamic cognitive flexibility/rigidity state. The modeling procedure presented here is able to estimate this dynamic slow process and leads to an improved RT prediction.

CONCLUSION

We proposed an EM algorithm to predict state variables of a state-space model with a Gamma distributed observation. The algorithm can be applied to a large class of behavioral signals, for which the observed variables are dynamic with a Gamma distribution. We have applied this to the problem of estimating a time-varying cognitive flexibility process on data derived from MSIT. This early result demonstrates the proposed methods potential to quantify cognitive dynamics through the course of the experiment. This is a powerful general framework for capturing moment-to-moment variation in human behavior. Its most immediate use is in better quantifying subjects' behavior during psychophysical experiments that involve reaction time, much as state-space models have done for learning. Further, this modeling technique has clinical implications. Because it is sensitive to immediate changes in behavior, it could quantify sharp changes in subjects' mental state, e.g. in response to a brain stimulation intervention. Finally, because the extracted state is defined at all times, it can be a substrate for neural decoding analyses similar to those commonly used in brain computer interface applications. Thus, this single algorithm has uses throughout the basic and clinical neurosciences.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for monitoring a mental state of a subject, the system comprising:
 a plurality of sensors configured to acquire physiological data and behavioral data from the subject;
 a processor configured to:
  i) receive calibration data acquired using the plurality of sensors while the subject is performing a task;
  ii) apply, using the calibration data, a state-space framework to determine a plurality of decoder parameters correlating brain activity and behavior with a mental state of the subject;
  iii) identify the mental state of the subject using the decoder parameters;
  iv) generate a report indicating the mental state of the subject and a brain stimulation designed to treat a brain condition of the subject; and
 an output for displaying the report.

2. The system of claim 1, wherein the mental state comprises a cognitive flexibility.

3. The system of claim 1, wherein the physiological data comprises neural data indicative of a brain activity of the subject.

4. The system of claim 3, wherein the processor is further configured to apply a linear-Gaussian model or a Bayesian model using the neural data.

5. The system of claim 1, wherein the processor is further configured to apply a Bayesian filter using the behavioral data.

6. The system of claim 1, wherein the processor is further configured to generate, based on the identified mental state, the brain stimulation to treat the brain condition of the subject.

7. The system of claim 6, wherein the system further comprises a stimulation module configured to deliver the brain stimulation.

8. The system of claim 1, wherein the processor is further configured to repeat steps iii) and iv) using physiological data acquired in substantially real time.

9. The system of claim 8, wherein the processor is further configured to adapt the brain stimulation based on the mental state identified upon repeating steps iii) and iv).

10. A method for monitoring a mental state of a subject, the method comprising
   i) receiving physiological and behavioral data acquired using the plurality of sensors while the subject is performing a task;
   ii) applying, using the data, a state-space framework to determine a plurality of decoder parameters correlating brain activity and behavior with a mental state of the subject;
   iii) identifying the mental state of the subject using the decoder parameters; and
   iv) generating a report indicating the mental state of the subject and a brain stimulation designed to treat a brain condition of the subject.

11. The method of claim 10, wherein the mental state comprises a cognitive flexibility.

12. The method of claim 10, wherein the physiological data comprises neural data indicative of a brain activity of the subject.

13. The method of claim 12, wherein the method further comprises applying a linear-Gaussian model or a Bayesian model using the neural data.

14. The method of claim 10, wherein the method further comprises applying a Bayesian filter using the behavioral data.

15. The method of claim 10, wherein the method further comprises generating, based on the identified mental state, the brain stimulation to treat a brain condition of the subject.

16. The method of claim 10, wherein the method further comprises repeating steps iii) and iv) using physiological data acquired in substantially real time.

17. The method of claim 16, wherein the method further comprises adapting the brain stimulation based on the mental state identified upon repeating step iii).

18. A non-transitory, computer-readable medium having thereon instructions that, when executed by a processor, can generate a report for controlling a mental state of a subject, the instructions comprising:
   i) acquiring, using the plurality of sensors, calibration data while the subject is performing a task;
   ii) applying, using the calibration data, a state-space framework to determine a plurality of decoder parameters correlating brain activity and behavior with a mental state of the subject;
   iii) acquiring physiological data using the plurality of sensors;
   iv) identifying a mental state of the subject using the decoder parameters and acquired physiological data;
   v) determining, based on the identified mental state, a brain stimulation to treat a brain condition of the subject; and
   vi) generating a report indicative of the brain stimulation.

19. The computer-readable medium of claim 18, wherein the instructions further comprise repeating steps iv) and v) using physiological data acquired in substantially real time.

20. The computer-readable medium of claim 19, wherein the instructions further comprise adapting the brain stimulation based on the mental state identified upon repeating step iv).

* * * * *

UNITED STATES PATENT AND TRADEMARK OFFICE
CERTIFICATE OF CORRECTION

PATENT NO. : 11,241,188 B2
APPLICATION NO. : 15/740975
DATED : February 8, 2022
INVENTOR(S) : Alik Widge et al.

It is certified that error appears in the above-identified patent and that said Letters Patent is hereby corrected as shown below:

In the Specification

Column 8, Line 58, "prepatent" should be --prepotent--.

Column 10, Line 24, "information" should be --Information--.

Column 15, Line 66, "RFC" should be --PFC--.

Column 16, Line 38, "tear" should be --fear--.

Column 17, Line 13, "estimates and" should be --estimates $\hat{\theta}$ and--.

Column 19, Line 56, "300 ins" should be --300 ms--.

Column 20, Line 3, "time-resealing" should be --time-rescaling--.

Column 20, Line 32, "[0,1]" should be --[0,T]--.

Column 21, Line 37, "fixture" should be --future--.

Column 23, Line 31, ", iteration" should be --. For iteration--.

Column 23, EQ. (26.c), Line 54, "$W_{\kappa,\kappa-1|K} = E[\chi_\kappa\chi_\kappa\chi_{k-1} \| Y,\theta^{(l)}]$" should be
--$W_{\kappa,\kappa-1|K} = E[\chi_\kappa\chi_{k-1} \| Y,\theta^{(l)}]$--.

Column 25, EQ. (34.b), Line 15, "$A\kappa = \sigma_{\kappa|\kappa}^2 * \alpha_1^{(l)} * \sigma_{\kappa+1|\kappa}^{2-1}$" should be --  --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,241,188 B2

Column 25, Eq. (38.a), Line 44, " $K\left(\log v + 1 - \frac{\Gamma'(v)}{\Gamma(v)}\right) + \sum_{\kappa=1}^{K} \log(y_\kappa) - E(\log \mu_\kappa) - y_\kappa W(1/\mu_\kappa) = 0$ "

should be -- $K\left(\log v + 1 - \frac{\Gamma'(v)}{\Gamma(v)}\right) + \sum_{\kappa=1}^{K} \log(y_\kappa) - E(\log \mu_\kappa) - y_\kappa E(1/\mu_\kappa) = 0$ --.

Column 27, Line 14, "a₁" should be --$\alpha_1$--.

Column 27, Line 14, "a₀" should be --$\alpha_0$--.

Column 27, Line 15, "$\sigma_c^2$" should be --$\sigma_\varepsilon^2$--.

Column 28, Line 5, "WI" should be --RT--.